US009895272B2

(12) United States Patent
Schmidt et al.

(10) Patent No.: US 9,895,272 B2
(45) Date of Patent: *Feb. 20, 2018

(54) ABSORBENT ARTICLES WITH PRIMARY AND SECONDARY INDICATING

(75) Inventors: Mattias Schmidt, Idstein (DE); Miguel Alvaro Robles, Wyoming, OH (US); Donald Carroll Roe, West Chester, OH (US); Michael I. Divo, Friedrichsdorf (DE)

(73) Assignee: The Procter & Gamble Company, Cincinnati, OH (US)

( * ) Notice: Subject to any disclaimer, the term of this patent is extended or adjusted under 35 U.S.C. 154(b) by 545 days.

This patent is subject to a terminal disclaimer.

(21) Appl. No.: 12/646,414

(22) Filed: Dec. 23, 2009

(65) Prior Publication Data

US 2010/0168700 A1     Jul. 1, 2010

Related U.S. Application Data

(60) Provisional application No. 61/141,573, filed on Dec. 30, 2008.

(51) Int. Cl.
*A61F 13/42*     (2006.01)

(52) U.S. Cl.
CPC ........ *A61F 13/42* (2013.01); *A61F 2013/422* (2013.01)

(58) Field of Classification Search
CPC ............... A61F 13/42; A61F 2013/422; A61F 2013/426; A61F 2013/425; A61F 2013/427; A61F 2013/428; A61F 2013/429

USPC .................................................. 604/318, 361
See application file for complete search history.

(56) References Cited

U.S. PATENT DOCUMENTS

| | | | |
|---|---|---|---|
| 2,681,032 A | 6/1954 | Shaw | |
| 3,731,685 A * | 5/1973 | Eidus | ...................... A61F 13/42 116/206 |
| 4,022,211 A | 5/1977 | Timmons et al. | |
| 4,231,370 A | 11/1980 | Mroz et al. | |
| 4,327,731 A | 5/1982 | Powell | |
| 4,507,121 A | 3/1985 | Leung | |
| 4,681,576 A | 7/1987 | Colon et al. | |
| 4,705,513 A | 11/1987 | Sheldon et al. | |
| 4,738,674 A | 4/1988 | Todd et al. | |
| 4,743,238 A | 5/1988 | Colon et al. | |
| 4,834,733 A | 5/1989 | Huntoon et al. | |
| 4,895,567 A | 1/1990 | Colon et al. | |
| 4,931,051 A | 6/1990 | Castello | |
| 5,035,691 A | 7/1991 | Zimmel et al. | |

(Continued)

FOREIGN PATENT DOCUMENTS

| | | |
|---|---|---|
| DE | 85 06 388 U1 | 6/1985 |
| DE | 20 2006 008161 | 3/2007 |

(Continued)

OTHER PUBLICATIONS

Lambi Premium Diapers, shown on the Bella Baby Boutique website on Apr. 30, 2009.*

(Continued)

*Primary Examiner* — Peter S Vasat
(74) *Attorney, Agent, or Firm* — James T. Fondriest; Kathleen Y. Carter

(57) ABSTRACT

An absorbent article with a primary visual fullness indicator and a secondary visual wetness indicator.

14 Claims, 12 Drawing Sheets

(56) References Cited

U.S. PATENT DOCUMENTS

| | | | |
|---|---|---|---|
| 5,066,711 A | 11/1991 | Colon et al. | |
| 5,078,708 A | 1/1992 | Haque | |
| 5,089,548 A | 2/1992 | Zimmel et al. | |
| 5,167,652 A | 12/1992 | Mueller | |
| 5,197,958 A | 3/1993 | Howell | |
| 5,342,861 A | 8/1994 | Raykovitz | |
| 5,354,289 A | 10/1994 | Mitchell et al. | |
| H1376 H | 11/1994 | Osborn et al. | |
| 5,435,010 A | 7/1995 | May | |
| 5,562,646 A * | 10/1996 | Goldman et al. | 604/368 |
| 5,647,863 A | 7/1997 | Hammons et al. | |
| 5,690,624 A | 11/1997 | Sasaki et al. | |
| 5,766,212 A | 6/1998 | Jitoe et al. | |
| 5,947,943 A | 9/1999 | Lee | |
| 6,075,178 A | 6/2000 | LaWilhelm et al. | |
| 6,284,942 B1 | 9/2001 | Rabin | |
| 6,297,424 B1 | 10/2001 | Olson et al. | |
| 6,307,119 B1 | 10/2001 | Cammarota et al. | |
| 6,515,194 B2 * | 2/2003 | Neading et al. | 604/361 |
| 6,596,918 B1 | 7/2003 | Wehrle et al. | |
| 6,617,488 B1 | 9/2003 | Springer et al. | |
| 6,653,522 B1 | 11/2003 | Blumenthal et al. | |
| 6,710,221 B1 | 3/2004 | Pierce et al. | |
| 6,772,708 B2 | 8/2004 | Klofta et al. | |
| 6,904,865 B2 | 6/2005 | Klofta et al. | |
| 7,154,019 B2 | 12/2006 | Mishima et al. | |
| 7,159,532 B2 | 1/2007 | Klofta et al. | |
| 7,172,667 B2 | 2/2007 | Vergona | |
| 7,178,571 B2 | 2/2007 | Vergona | |
| 7,241,627 B2 | 7/2007 | Wilhelm et al. | |
| 7,280,441 B2 | 10/2007 | MacDonald et al. | |
| 7,306,764 B2 | 12/2007 | Mody | |
| 7,322,472 B2 | 1/2008 | Swiecicki et al. | |
| 7,332,642 B2 | 2/2008 | Liu | |
| 8,080,704 B2 | 12/2011 | Uchida et al. | |
| 2001/0008683 A1 | 7/2001 | Takai et al. | |
| 2002/0007162 A1 | 1/2002 | Cammarota et al. | |
| 2002/0062114 A1 | 5/2002 | Murai et al. | |
| 2002/0016579 A1 | 12/2002 | Stenberg | |
| 2003/0078553 A1 | 4/2003 | Wada et al. | |
| 2003/0130631 A1 | 7/2003 | Springer et al. | |
| 2004/0055367 A1 | 3/2004 | Swiecicki et al. | |
| 2004/0138633 A1 | 7/2004 | Mishima et al. | |
| 2004/0254549 A1 | 12/2004 | Olson et al. | |
| 2004/0254550 A1 * | 12/2004 | Huang et al. | 604/361 |
| 2005/0065489 A1 | 3/2005 | Driskell et al. | |
| 2005/0112085 A1 | 5/2005 | MacDonald et al. | |
| 2005/0124947 A1 | 6/2005 | Fernfors | |
| 2005/0136773 A1 * | 6/2005 | Yahiaoui | A61F 13/537 442/394 |
| 2006/0025733 A1 | 2/2006 | Kikuchi et al. | |
| 2006/0069362 A1 | 3/2006 | Odorzynski et al. | |
| 2006/0149197 A1 | 7/2006 | Niemeyer et al. | |
| 2006/0149204 A1 | 7/2006 | Niemeyer et al. | |
| 2006/0229577 A1 | 10/2006 | Roe et al. | |
| 2007/0197986 A1 | 8/2007 | Matsui | |
| 2007/0233027 A1 | 10/2007 | Roe et al. | |
| 2007/0276348 A1 | 11/2007 | Stenberg | |
| 2008/0071239 A1 | 3/2008 | Nandrea et al. | |
| 2008/0086060 A1 | 4/2008 | Kritzman et al. | |
| 2008/0147031 A1 | 6/2008 | Long et al. | |
| 2008/0208151 A1 | 8/2008 | Zacharias et al. | |
| 2008/0228157 A1 | 9/2008 | McKiernan et al. | |
| 2010/0168695 A1 | 7/2010 | Robles et al. | |
| 2010/0168696 A1 | 7/2010 | Robles et al. | |
| 2010/0168697 A1 | 7/2010 | Robles et al. | |
| 2010/0168698 A1 | 7/2010 | Robles et al. | |
| 2010/0168699 A1 | 7/2010 | Robles et al. | |
| 2010/0168700 A1 | 7/2010 | Schmidt et al. | |
| 2010/0168701 A1 | 7/2010 | Schmidt et al. | |

FOREIGN PATENT DOCUMENTS

| | | |
|---|---|---|
| EP | 0 705 089 B1 | 5/1997 |
| EP | 0 925 769 A2 | 6/1999 |
| EP | 1 216 673 B1 | 10/2005 |
| FR | 2 695 824 B1 | 3/1994 |
| JP | 2000-093455 A | 4/2000 |
| JP | 2001-095845 | 4/2001 |
| JP | 2005-127933 A2 | 5/2005 |
| JP | 2006-341020 A | 12/2006 |
| KR | 98039173 | 8/1998 |
| KR | 100484478 B1 | 4/2005 |
| WO | WO 95/00099 A1 | 1/1995 |
| WO | WO 99/16401 | 4/1999 |
| WO | WO 99/56690 A1 | 11/1999 |
| WO | WO 01/95845 A1 | 12/2001 |
| WO | WO 2005/030084 A2 | 4/2005 |
| WO | WO 2005/039656 A1 | 5/2005 |
| WO | WO 2005/102238 A1 | 11/2005 |
| WO | WO 2006/110428 A1 | 10/2006 |
| WO | WO 2008/072116 A1 | 6/2008 |
| WO | WO 2008/072118 A1 | 6/2008 |

OTHER PUBLICATIONS

International Search Report, PCT/US2009/069579, dated Apr. 22, 2010, 12 pages.
International Search Report, PCT/US2009/069570, dated Apr. 22, 2010, 12 pages.
International Search Report, PCT/US2009/069572, dated Jul. 5, 2010, 16 pages.
International Search Report, PCT/US2009/069659, dated Jul. 6, 2010, 17 pages.
International Search Report, PCT/US2009/069656, dated Jul. 6, 2010, 17 pages.
U.S. Appl. No. 12/646,296, filed Dec. 23, 2009, Robles, et al.
U.S. Appl. No. 12/646,315, filed Dec. 23, 2009, Robles, et al.
U.S. Appl. No. 12/646,334, filed Dec. 23, 2009, Robles, et al.
U.S. Appl. No. 12/646,354, filed Feb. 23, 2009, Robles, et al.
U.S. Appl. No. 12/646,393, filed Dec. 23, 2009, Robles, et al.
U.S. Appl. No. 12/646,430, filed Dec. 23, 2009, Schmidt, et al.
All Office Actions, U.S. Appl. No. 12/646,296.
All Office Actions, U.S. Appl. No. 12/646,315.
All Office Actions, U.S. Appl. No. 12/646,334.
All Office Actions, U.S. Appl. No. 12/646,354.
All Office Actions, U.S. Appl. No. 12/646,414.
All Office Actions, U.S. Appl. No. 12/646,430.
International Search Report, PCT/US2009/069569, dated May 19, 2010, 17 pages.
International Search Report, PCT/US2009/069559, dated Feb. 17, 2010, 12 pages.

* cited by examiner

ABSORBENT ARTICLES WITH PRIMARY AND SECONDARY INDICATING

CROSS REFERENCE TO RELATED APPLICATIONS

This application claims the benefit of U.S. provisional patent application 61/141,573 filed Dec. 30, 2008, the substance of which is hereby incorporated by reference.

FIELD

In general, embodiments of the present disclosure relate to wetness indicating for absorbent articles. In particular, embodiments of the present disclosure relate to visual fullness indicating for absorbent articles.

BACKGROUND

Absorbent articles can absorb liquid bodily exudates such as sweat, blood, urine, menses, etc. An absorbent article can include a wetness indicator. The wetness indicator can indicate the presence of a liquid bodily exudate in the article. Unfortunately, some wetness indicators for absorbent articles can be difficult to understand. If the signal from a wetness indicator is misunderstood then the absorbent article may be changed too soon. The wearer may underutilize the capacity of the article. If the signal from a wetness indicator is misunderstood then the absorbent article may be changed too late. The bodily exudates may exceed the capacity of the article resulting in leaks.

SUMMARY

Figure 1A:
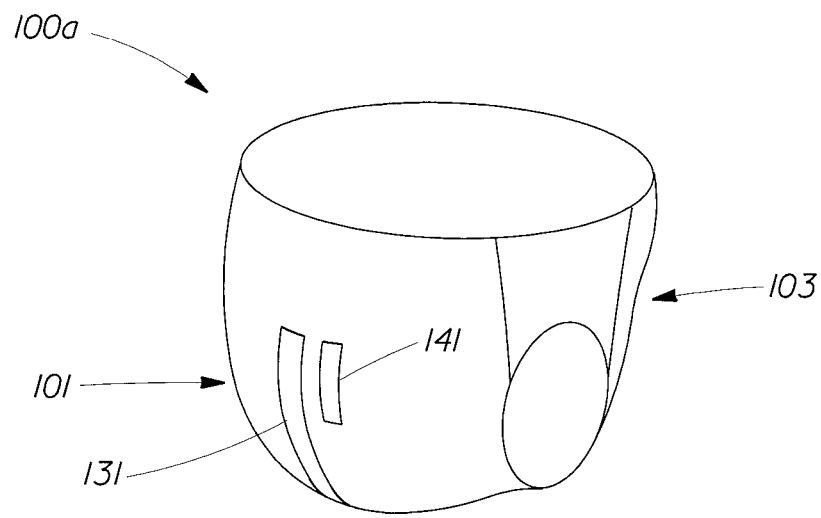
FIG. 1A illustrates a pant-type disposable wearable absorbent article with a primary visual fullness indicator and a secondary visual wetness indicator in the front, according to embodiments of the present disclosure.

The present disclosure includes absorbent articles with indicators that are easy to understand. The absorbent articles of the present disclosure are easy to understand because they have primary visual fullness indicators and secondary visual wetness indicators.

As an example, an absorbent article can have a primary visual fullness indicator and a secondary visual wetness indicator. The indicators can change visual states in sequence. First the primary visual fullness indicator can begin to change visual states, providing a primary indicating signal. The primary signal can indicate that the absorbent article is somewhat filled. Second, the secondary visual wetness indicator can begin to change visual states, providing a secondary indicating signal that is separate from and in addition to the primary indicating signal. The secondary indicating signal can indicate that the absorbent article is approaching full. The combination of the primary indicating signal and the secondary indicating signal can be easily understood as indicating degrees of fullness. Together, the combination of a primary visual fullness indicator and a secondary visual wetness indicator can be considered a visual fullness indicating system.

An absorbent article having a primary visual fullness indicator and a secondary visual wetness indicator can help provide certainty about the fullness of the absorbent article. By knowing how full an article is, the article can be changed after the wearer has appropriately utilized the capacity of the article. Also, by knowing how full an article is, the article can be changed before it is likely to leak.

DETAILED DESCRIPTION

The primary and secondary indicators of the present disclosure can be used with all kinds of absorbent articles.

An absorbent article can absorb liquid bodily exudates such as sweat, blood, urine, menses, etc. An absorbent article can be a product or a material. Examples of absorbent articles include products and/or materials for sanitary protection, hygienic use, and/or wound care.

Some absorbent articles are disposable. A disposable absorbent article is configured to be partly or wholly disposed of after a single use. A disposable absorbent article is configured such that the soiled article, or a soiled portion of the article, is not intended to be restored and reused (e.g., not intended to be laundered). Examples of disposable absorbent articles include wound care products, such as bandages and dressings, as well as feminine care products, such as pads and liners. Disposable absorbent articles can use embodiments of the present disclosure.

Some absorbent articles are wearable. A wearable absorbent article is configured to be worn on or around a body of a wearer. Wearable absorbent articles can also be disposable. Examples of disposable wearable absorbent articles include disposable diapers and disposable incontinence undergarments. A disposable wearable absorbent article can receive and contain bodily exudates while being worn by a wearer. In some embodiments, a disposable wearable absorbent article can include a topsheet, an absorbent core, an outer cover, a waist opening, and leg openings. Disposable wearable absorbent articles can use embodiments of the present disclosure.

One kind of wetness indicator for an absorbent article is a visual fullness indicator. A wetness indicator is considered visual if it can indicate the presence of a liquid bodily exudate by its visual state. Throughout the present disclosure, unless otherwise stated, the presence of a liquid bodily exudate refers to the presence of a concentration of the liquid bodily exudate that is sufficient to cause a visual wetness indicator to change visual states. A wetness indicator is considered a fullness indicator if it can indicate the degree to which a liquid bodily exudate has filled an absorbent article. A visual fullness indicator can indicate the presence of a liquid bodily exudate by a wet edge that moves along the indicator such that the indicator progressively changes visual states. A visual fullness indicator can include one or more visual indicating areas. A visual indicating area is a defined continuous two-dimensional region, configured to indicate the presence of a liquid bodily exudate by its visual state. As examples, in various embodiments, an indicator can comprise a series of indicating areas or a pattern of indicating areas.

The figures of the present disclosure are intended to illustrate elements, their parts, and their relationships, as described in the specification; the figures are not intended to illustrate any particular relative or absolute size or dimension, unless otherwise stated in the text.

FIGS. 1A-2C illustrate various disposable wearable absorbent articles, each with one or more indicators. For clarity, FIGS. 1A-2C do not illustrate all details of the indicators or of the disposable wearable absorbent articles. Each primary indicator in FIGS. 1A-2C can be any embodiment of a primary indicator of the present disclosure. Each secondary indicator in FIGS. 1A-2C can be any embodiment of a secondary indicator of the present disclosure.

FIG. 1A illustrates an outside perspective view of a front 101 and a side 103 of a pant-type disposable wearable absorbent article 100A formed for wearing. The absorbent article 100A includes a longitudinally oriented primary visual fullness indicator 131 and a secondary visual wetness indicator 141 disposed in the front 101. Together, the primary visual fullness indicator 131 and the secondary visual wetness indicator 141 can be considered a visual fullness indicating system.

Throughout the present disclosure, a reference to a pant-type disposable wearable absorbent article can refer to an embodiment that is side-fastenable or to an embodiment without fasteners. A reference to a pant-type disposable wearable absorbent article can also refer to an article with preformed waist and/or leg openings or to an embodiment that is not preformed. Thus, each embodiment of an absorbent article of the present disclosure that is described as pant-type can be configured in any of these ways, as will be understood by one of ordinary skill in the art.

Figure 1B:
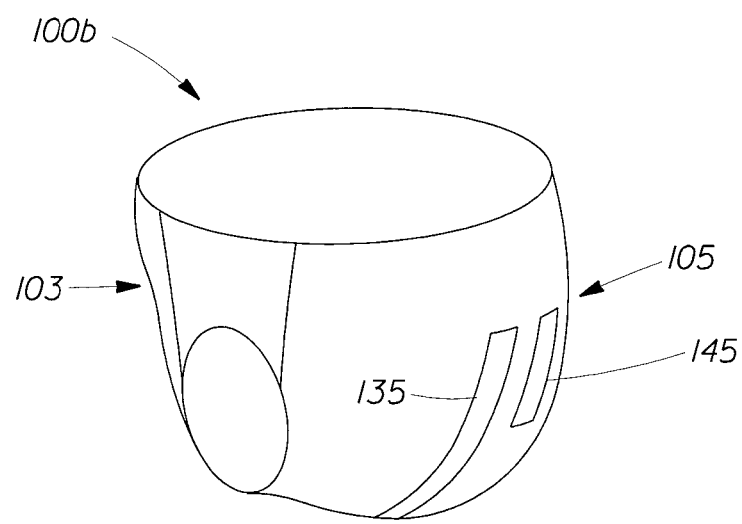
FIG. 1B illustrates a pant-type disposable wearable absorbent article with a primary visual fullness indicator and a secondary visual wetness indicator in the back, according to embodiments of the present disclosure.

FIG. 1B illustrates an outside perspective view of a side 103 and a back 105 of a pant-type disposable wearable absorbent article 100B formed for wearing. The absorbent article 100B includes a longitudinally oriented primary visual fullness indicator 135 and a secondary visual wetness indicator 145 disposed in the back 105. Together, the primary visual fullness indicator 135 and the secondary visual wetness indicator 145 can be considered a visual fullness indicating system.

Figure 1C:
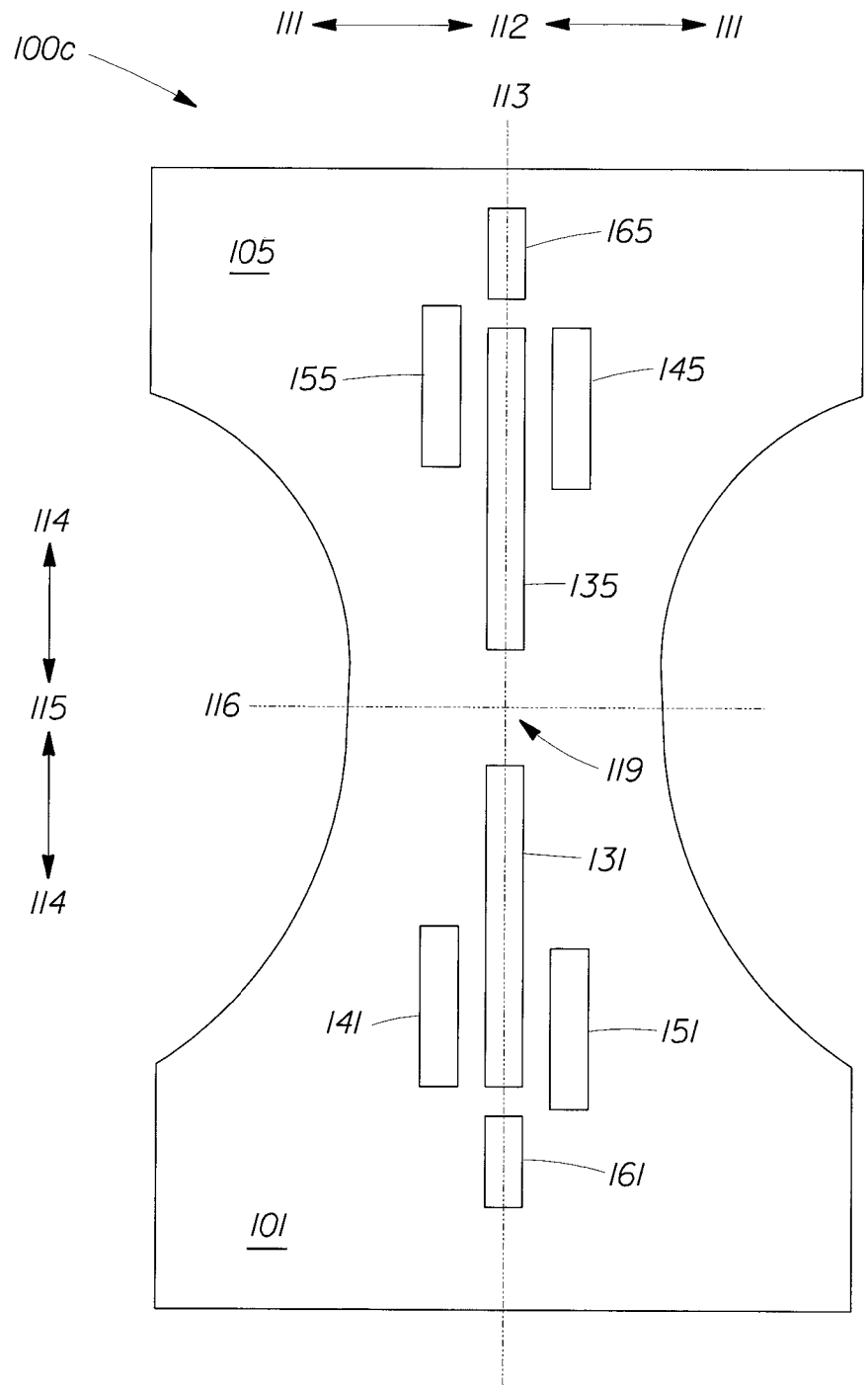
FIG. 1C illustrates a pant-type disposable wearable absorbent article with a number of primary visual fullness indicators and secondary visual wetness indicators, according to embodiments of the present disclosure.

FIG. 1C illustrates an outside plan view of a pant-type disposable wearable absorbent article 100C laid out flat. The disposable wearable absorbent article 100C includes a front 101 and a back 105, which are separated by a lateral centerline 116.

In FIG. 1C, a longitudinal centerline 113 and the lateral centerline 116 provide lines of reference for referring to relative locations of the disposable wearable absorbent article 100C. When a first location is nearer to the longitudinal centerline 113 than a second location, the first location can be considered laterally inboard 112 to the second location. Similarly, the second location can be considered laterally outboard 111 from the first location. When a third location is nearer to the lateral centerline 116 than a fourth location, the third location can be considered longitudinally inboard 115 to the fourth location. Also, the fourth location can be considered longitudinally outboard 114 from the third location.

A reference to an inboard location, without a lateral or longitudinal limitation, refers to a location of the disposable wearable absorbent article 100C that is laterally inboard and/or longitudinally inboard to another location. In the same way, a reference to an outboard location, without a lateral or longitudinal limitation, refers to a location of the disposable wearable absorbent article 100C that is laterally outboard and/or longitudinally outboard from another location.

Inboard and outboard can also be understood with reference to a center of a disposable wearable absorbent article. The longitudinal centerline 113 and the lateral centerline 116 cross at a center 119 of the disposable wearable absorbent article 100C. When one location is nearer to the center 119 than another location, the one location can be considered inboard to the other location. The one location can be inboard laterally, or longitudinally, or both laterally and longitudinally. The other location can be considered outboard from the one location. The other location can be outboard laterally, or longitudinally, or both laterally and longitudinally.

FIG. 1C includes arrows indicating relative directions for laterally outboard 111, laterally inboard 112, longitudinally outboard 114, and longitudinally inboard 115, each with respect to the disposable wearable absorbent article 100C. Throughout the present disclosure, a reference to a longitudinal dimension, measurement, line, or direction refers to a dimension, measurement, line, or direction that is substantially or completely parallel to the longitudinal centerline 113 and a reference to a lateral dimension, measurement, line, or direction refers to a dimension, measurement, line, or direction that is substantially or completely parallel to the lateral centerline 116. The terminology for describing relative locations, as discussed above, is used for disposable wearable absorbent articles throughout the present disclosure. This terminology can also be similarly applied to various other absorbent articles, as will be understood by one of ordinary skill in the art.

The disposable wearable absorbent article 100C includes a number of indicators in various exemplary locations and orientations. The disposable wearable absorbent article 100C includes a primary longitudinally oriented visual fullness indicator 131, along the longitudinal centerline 113 in the front 101. The front 101 also includes a first secondary visual wetness indicator 141, a second secondary visual wetness indicator 151, and a third secondary visual wetness indicator 161. Together, the primary visual fullness indicator 131 and one or more of the secondary visual wetness indicators 141, 151, and 161 can be considered a visual fullness indicating system.

The disposable wearable absorbent article 100C also includes another longitudinally oriented primary visual fullness indicator 135, along the longitudinal centerline 113 in the back 105. The back 105 also includes a fourth secondary visual wetness indicator 145, a fifth secondary visual wetness indicator 155, and a sixth secondary visual wetness indicator 165. Together, the primary visual fullness indicator 135 and one or more of the secondary visual wetness indicators 145, 155, and 165 can be considered a visual fullness indicating system.

In the disposable wearable absorbent article 100C, the indicators are oriented substantially radially out from the center 119. However, in addition to the locations and orientations illustrated in FIG. 1C, a visual fullness indicator of the present disclosure can be disposed in various alternate locations and orientations in an absorbent article, as will be understood by one of ordinary skill in the art. As an example, a visual fullness indicator can be disposed in a pant-type disposable wearable absorbent article in a lateral orientation or at an angle with respect to a centerline of the article.

Figure 2A:
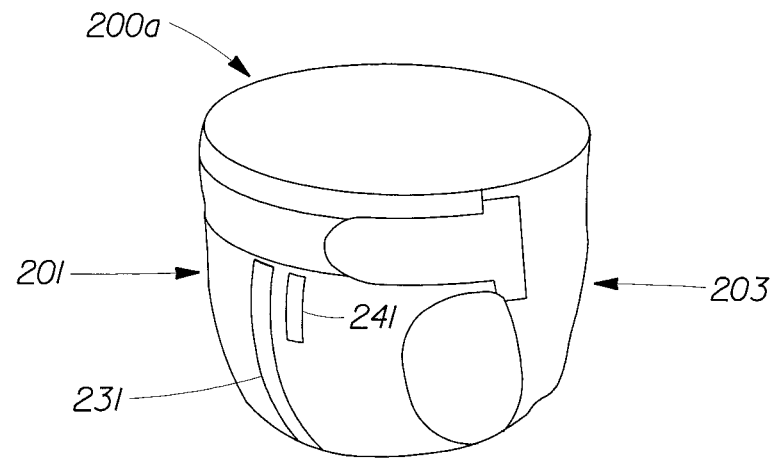
FIG. 2A illustrates a front-fastenable disposable wearable absorbent article with a primary visual fullness indicator and a secondary visual wetness indicator in the front, according to embodiments of the present disclosure.

FIG. 2A illustrates an outside perspective view of a front 201 and a side 203 of a front-fastenable disposable wearable absorbent article 200A formed for wearing. The absorbent article 200A includes a primary longitudinally oriented visual fullness indicator 231 and a secondary visual wetness indicator 241 disposed in the front 201. Together, the primary visual fullness indicator 231 and the secondary visual wetness indicator 241 can be considered a visual fullness indicating system.

While the present disclosure refers to front-fastenable absorbent articles, the present disclosure also contemplates alternate embodiments of absorbent articles having primary visual fullness indicators and secondary visual wetness indicators, as described herein, wherein the absorbent articles are rear-fastenable. Thus, each embodiment of an absorbent article of the present disclosure that is described as front-fastenable can also be configured to be rear fastenable, as will be understood by one of ordinary skill in the art.

Figure 2B:
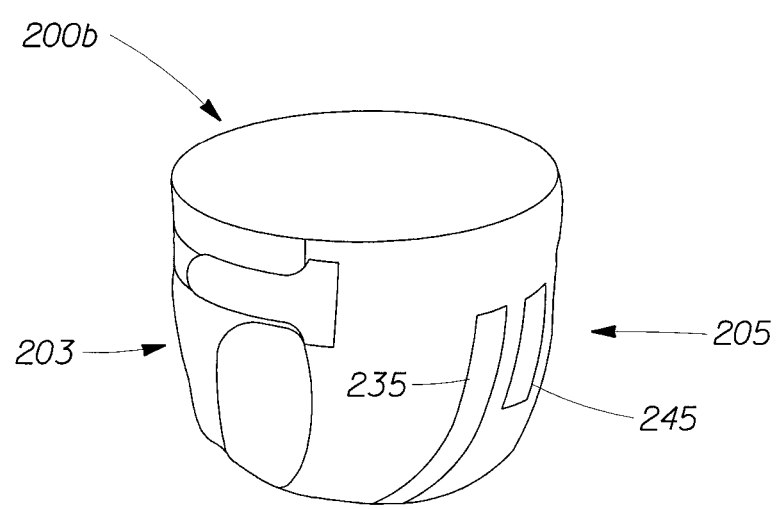
FIG. 2B illustrates a front-fastenable disposable wearable absorbent article with a primary visual fullness indicator and a secondary visual wetness indicator in the back, according to embodiments of the present disclosure.

FIG. 2B illustrates an outside perspective view of a side 203 and a back 205 of a front-fastenable disposable wearable absorbent article 200B formed for wearing. The absorbent article 200B includes a longitudinally oriented primary visual fullness indicator 235 and a secondary visual wetness indicator 245 disposed in the back 205. Together, the primary visual fullness indicator 235 and the secondary visual wetness indicator 245 can be considered a visual fullness indicating system.

Figure 2C:
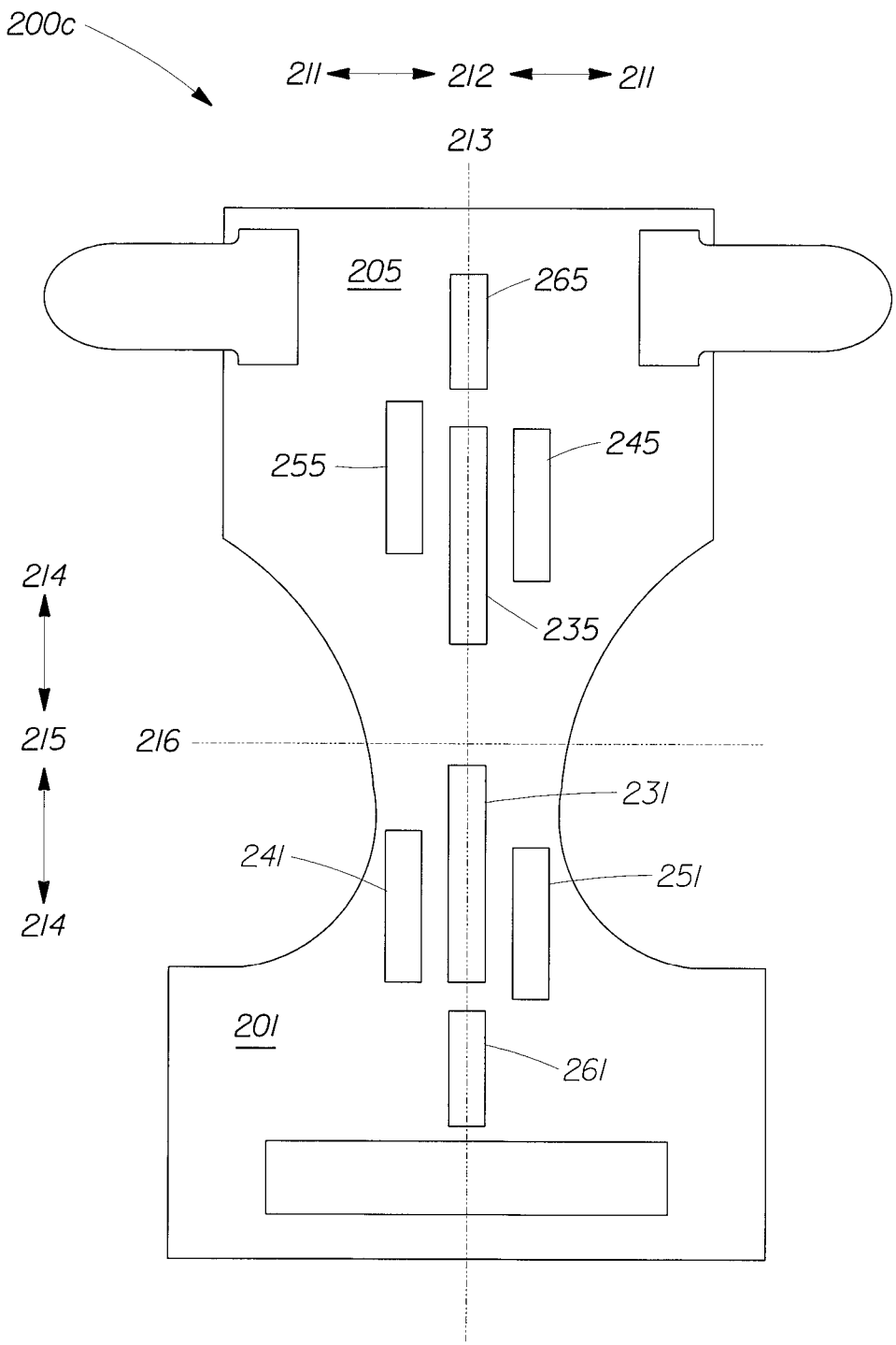
FIG. 2C illustrates a front-fastenable disposable wearable absorbent article with a number of primary visual fullness indicators and secondary visual wetness indicators, according to embodiments of the present disclosure.

FIG. 2C illustrates an outside plan view of a front-fastenable disposable wearable absorbent article 200C laid out flat. The disposable wearable absorbent article 200C includes a front 201, a back 205, a longitudinal centerline 213, and a lateral centerline 216.

The disposable wearable absorbent article 200C includes a number of indicators in various exemplary locations and orientations. The disposable wearable absorbent article 200C includes a primary longitudinally oriented visual fullness indicator 231, along the longitudinal centerline 213 in the front 201. The front 201 also includes a first secondary visual wetness indicator 241, a second secondary visual wetness indicator 251, and a third secondary visual wetness indicator 261. Together, the primary visual fullness indicator 231 and one or more of the secondary visual wetness indicators 241, 251, and 261 can be considered a visual fullness indicating system.

The disposable wearable absorbent article 200C also includes a longitudinally oriented primary visual fullness indicator 235, along the longitudinal centerline 213 in the back 205. The back 205 also includes a first secondary wetness indicator 245, a second secondary wetness indicator 255, and a third secondary wetness indicator 265. Together, the primary visual fullness indicator 235 and one or more of the secondary visual wetness indicators 245, 255, and 265 can be considered a visual fullness indicating system.

In the disposable wearable absorbent article 200C, the indicators are oriented substantially radially out from the center 219. However, in addition to the locations and orientations illustrated in FIG. 2C, a visual fullness indicator of the present disclosure can be disposed in various alternate locations and orientations in an absorbent article, as will be understood by one of ordinary skill in the art. As an example, a visual fullness indicator can be disposed in a front-fastenable disposable wearable absorbent article in a lateral orientation or at an angle with respect to a centerline of the article.

Figure 3A:
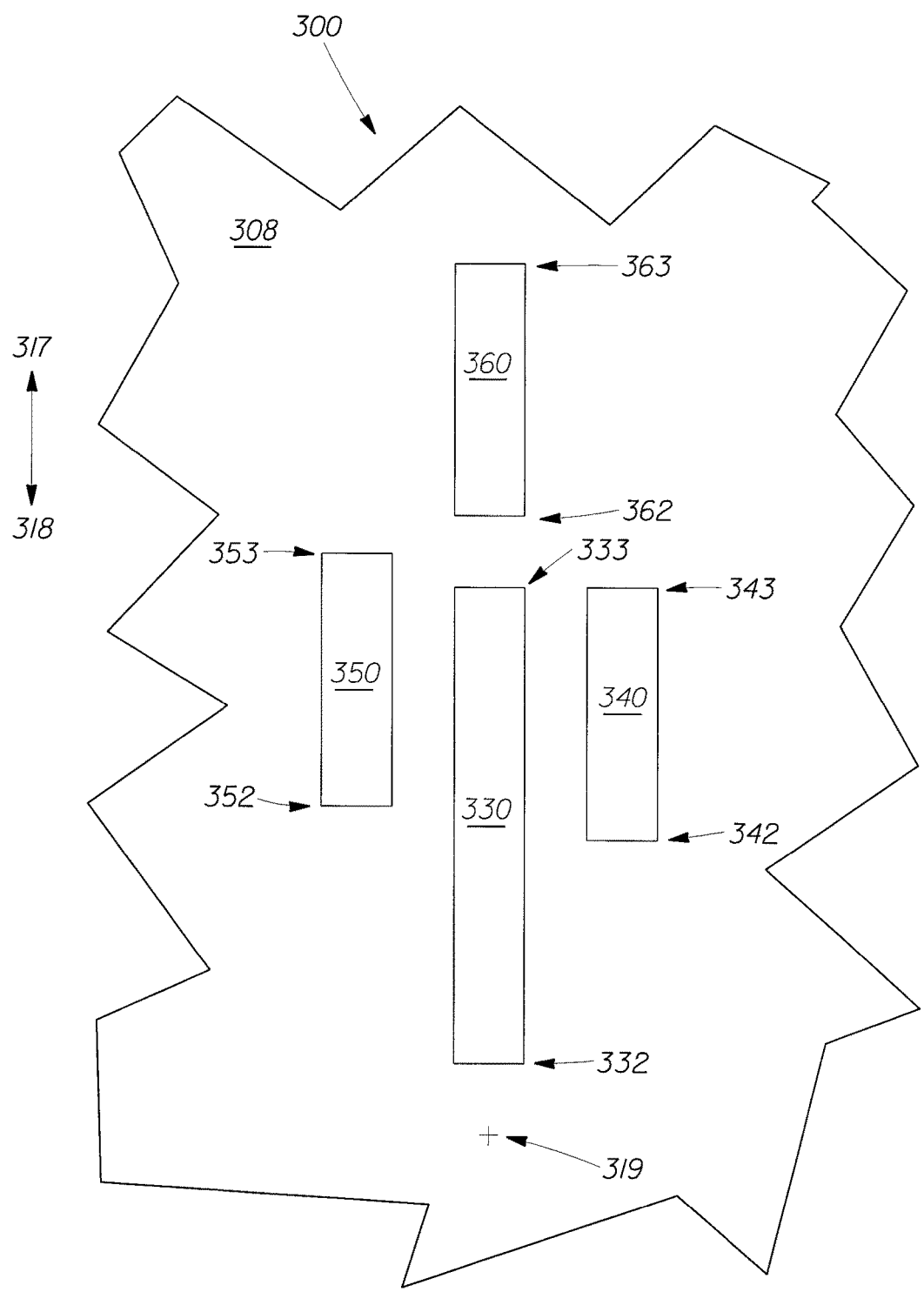
FIG. 3A illustrates a portion of an absorbent article with a primary visual fullness indicator and three secondary visual wetness indicators, according to embodiments of the present disclosure.

FIG. 3A illustrates an outside plan view of a portion 308 of an absorbent article 300 laid out flat. In various embodiments, the absorbent article 300 can be a disposable wearable absorbent article, such as a pant-type disposable wearable absorbent article or a front-fastenable disposable wearable absorbent article. In FIG. 3A, outside edges of the portion 308 are broken lines, since the portion 308 is illustrated as separate from the rest of the absorbent article 300. For reference, FIG. 3A illustrates a center 319 of the absorbent article 300 and arrows indicating relative directions for outboard 317 and inboard 318 for the absorbent article 300.

The portion 308 of the absorbent article 300 includes a primary visual fullness indicator 330. A primary indicator is considered primary with respect to a secondary indicator because it can begin to change states before a secondary indicator begins to change states.

The primary visual fullness indicator 330 is disposed offset from the center 319. In various embodiments, one or more parts of an indicator can be disposed near, at, or overlapping a center of an absorbent article. For example, a single indicating area can extend from a front of an absorbent article, through the center of the absorbent article, to the back of the absorbent article. In such an embodiment, a farthest inboard point along the indicating area can be considered an inboard end of two indicators.

The primary visual fullness indicator 330 includes an inboard end 332 and an outboard end 333. The primary visual fullness indicator 330 has an overall indicator length measured along the primary visual fullness indicator 330 from the inboard end 332 to the outboard end 333. The primary visual fullness indicator 330 has an overall shape that is substantially elongated and substantially rectangular. The primary visual fullness indicator 330 has a substantially uniform width along its entire overall indicator length.

In various embodiments an indicator and/or an indicating area can have an overall shape that is more or less elongated. In some embodiments, part, or parts, or all of an indicator and/or an indicating area can be straight, curved, angled, segmented, or any regular or irregular geometric shape (such as a square, rectangle, triangle, trapezoid, octagon, hexagon, star, half circle, a quarter circle, a half oval, a quarter oval, a radial pattern, etc.), a recognizable image (such as a letter, number, word, character, face of an animal, face of a person, etc.), or another recognizable image (such as a plant, a car, etc.), or another shape, or combinations of any of these shapes. Also, in various embodiments, an indicator and/or an indicating area can have varying widths over part, or parts, or all of its length.

A visual fullness indicator is a visually distinct and recognizable pathway of one or more visual indicators and/or visual indicating areas. A pathway is recognizable in its visual context. In other words, a pathway is distinct, when compared with the appearance of a surrounding area.

The pathway of a visual fullness indicator has two defined ends, a middle between the two ends, and a defined length from its one end to its other end. A visual fullness indicator can have one or more widths, each of which is less than its defined length.

A visual fullness indicator can be configured in various forms. For example, a visual fullness indicator can be formed by a single, continuous indicating area disposed along a pathway. As another example, a visual fullness indicator can be formed by a plurality of discrete indicators and/or discrete indicating areas disposed along a pathway.

The primary visual fullness indicator 330 includes one visual fullness indicating area. In various embodiments, an indicator can include one or more visual fullness indicating areas.

The primary visual fullness indicator 330 is in fluid communication with an absorbent core of the absorbent article 300 along its entire overall indicator length. In various embodiments, a visual indicator can be configured such that part, or parts, or substantially all, or all of the indicator is in fluid communication with an absorbent core. In some embodiments, a visual indicator can be configured such that part, or parts, or substantially all, or all of the indicator overlaps an absorbent core or such that part, or parts, or substantially all, or all of the indicator does not overlap an absorbent core.

Throughout the present disclosure, fluid communication refers to a configured structural relationship that allows a liquid substance to freely pass from one element or location to another element or location; however, one element or location is not necessarily considered to be in fluid communication with another element or location merely by being connected or joined to a common element through which liquid can possibly pass. This definition of fluid communication is further explained by the following examples.

For example, if one element is configured to be in direct physical contact with another element such that a liquid substance can freely pass from the one element through the contacting portions to the other element, then the elements can be considered to be in fluid communication. As another example, if one element is connected to another element by a means for fluid communication such that a liquid substance can freely pass from the one element through the means for fluid communication to the other element, then the elements can be considered to be in fluid communication.

As a further example, if one element is connected to a substrate and another element is connected to the same substrate, but the substrate does not allow a liquid substance to freely pass through, then the elements are considered to be out of fluid communication. This holds true even if liquid can possibly pass through the substrate, so long as the liquid cannot pass through freely. The above definition of fluid communication, as explained through these examples, will be understood by one of ordinary skill in the art.

Throughout the present disclosure, the term liquid bodily exudate refers to any bodily substances exuded in liquid form (e.g. urine) and/or any liquid-like bodily substances (e.g. runny feces).

The primary visual fullness indicator 330 is configured to change from one or more initial visual states to one or more subsequent visual states when indicating the presence of a liquid bodily exudate. Throughout the present disclosure, the term visual state refers to an appearance which can be perceived by an unaided human with normal vision in standard lighting conditions. A visual state can comprise one or more colors, variations of color(s), patterns, letters, numbers, symbol, designs, images, and/or other visual devices. Colors include well known colors such as red, orange, yellow, green, blue, purple, etc. Variations of a color include variations in chroma, hue, and brightness, among others. While these informal terms are used for ease of reference, embodiments of the present disclosure are intended to encompass all colors which can be perceived by an unaided human with normal vision in standard lighting conditions.

In various embodiments, part, or parts, or all of a visual fullness indicating area can be configured to change from one or more initial visual states to one or more subsequent visual states. Also, in embodiments of the present disclosure, for a particular portion of a visual fullness indicating area, an initial visual state and a subsequent visual can each be any visual state, no long as the subsequent visual state is visually distinguishable from the first initial visual state.

Throughout the present disclosure, visual states are considered visually distinguishable if they can be recognized as different on sight by an unaided human with normal vision in standard lighting conditions. As an example, an unaided human with normal vision in standard lighting conditions should be able to recognize blue and yellow as different colors on sight. Thus, the blue and the yellow would be considered visually distinguishable visual states. As another example, an unaided human with normal vision in standard lighting conditions may be able to recognize a light shade of orange and a dark shade of orange as different shades of a color on sight. Thus, the light shade of orange and the dark shade of orange would be considered visually distinguishable visual states. As a further example, an unaided human with normal vision in standard lighting conditions may be able to recognize a first pattern and a second pattern as different visual states on sight. Thus, the first pattern and the second pattern would be considered visually distinguishable visual states.

As a still further example, an unaided human with normal vision in standard lighting conditions should be able to recognize an area with letters and a blank area as different visual states on sight. Thus, the area with letters and the blank area would be considered visually distinguishable visual states. Similarly, an area with numbers, symbols, designs, images, and/or other visual devices would also be considered visually distinguishable from a blank area or from a uniformly colored area. In addition to these examples, there are many other possible visually distinguishable visual states, as will be understood by one or ordinary skill in the art.

There are several ways by which absorbent articles of the present disclosure can be configured to include visual indicators that change visual states when indicating the presence of a bodily exudate, as will be understood by one of ordinary skill in the art. For example, an absorbent article can be configured to include such visual fullness indicators as described in the following US patents: U.S. Pat. No. 4,022, 211, entitled "Wetness indicator for absorbent pads" issued on May 10, 1977 to Timmons, et al.; U.S. Pat. No. 4,231, 370, entitled "Disposable diaper type garment having wetness indicator" issued on Nov. 4, 1980 to Mroz, et al.; U.S. Pat. No. 4,327,731, entitled "Moisture indicator" issued on May 4, 1982 to Powell; U.S. Pat. No. 4,681,576, entitled "Wetness indicating hot-melt adhesive" issued on Jul. 21, 1987 to Colon, et al.; U.S. Pat. No. 4,705,513, entitled "Disposable diaper with wetness indicator" issued on Nov. 10, 1987 to Sheldon, et al.; U.S. Pat. No. 4,738,674, entitled "Moisture indicator apparatus and method" issued on Apr. 19, 1988 to Todd, et al.; U.S. Pat. No. 4,743,238, entitled "Wetness indicating hot-melt adhesive" issued on May 10, 1988 to Colon et al.; U.S. Pat. No. 4,895,567, entitled "Wetness indicating hot-melt adhesive" issued on Jan. 23, 1990 to Colon et al.; U.S. Pat. No. 4,931,051, entitled "Wetness indicator" issued on Jun. 5, 1990 to Castello; U.S. Pat. No. 5,035,691, entitled "Hot melt moisture indicator material for disposable articles" issued on Jul. 30, 1991 to Zimmel, et al.; U.S. Pat. No. 5,066,711, entitled "Wetness indicating hot-melt adhesive" issued on Nov. 19, 1991 to Colon et al.; U.S. Pat. No. 5,089,548, entitled "Hot melt moisture indicator material for disposable articles" issued on Feb. 18, 1992 to Zimmel, et al.; U.S. Pat. No. 5,167,652, entitled "Moisture sensitive film" issued on Dec. 1, 1992 to Mueller; U.S. Pat. No. 5,342,861, entitled "Hot melt wetness indicator" issued on Aug. 30, 1994 to Raykovitz; U.S. Pat. No. 5,354,289 entitled "Absorbent product including super absorbent material and fluid absorption capacity monitor" issued on Oct. 11, 1994 to Mitchell, et al.; H1,376, entitled "Capacity indicia for absorbent articles" issued on Nov. 1, 1994 to Osborne, et al.; U.S. Pat. No. 5,647,863, entitled "Absorbent article with clean appearance and capacity signal means" issued on Jul. 15, 1997 to Hammons, et al.; U.S. Pat. No. 5,690,624, entitled "Disposable diaper" issued on Nov. 25, 1997 to Sasaki, et al.; U.S. Pat. No. 5,766,212, entitled "Disposable diaper" issued on Jun. 16, 1998 to Jitoe, et al.; U.S. Pat. No. 6,075,178, entitled "Absorbent article with wetness indicator" issued on Jun. 13, 2000; U.S. Pat. No. 6,515,194, entitled "Diaper having centrally-located chromatographic layer with peripherally-located wetness indicator" issued on Feb. 4, 2003 to Neading, et al.; U.S. Pat. No. 6,596,918, entitled "Absorbent articles having wetness indicating graphics and employing masking techniques" issued on Jul. 22, 2003 to Wehrle, et al.; U.S. Pat. No. 6,653,522, entitled "Hot melt adhesives based on sulfonated polyesters comprising wetness indicator" issued on Nov. 25, 2003 to Blumenthal, et al.; U.S. Pat. No. 6,772,708, entitled "Wetness indicator having improved colorant retention" issued on Aug. 10, 1994 to Klofta, et al.; U.S. Pat. No. 6,904,865, entitled "Wetness indicator having improved colorant retention and durability" issued on Jun. 14, 2005 to Klofta, et al.; U.S. Pat. No. 7,159,532, entitled "Wetness indicator having improved colorant retention and durability" issued on Jan. 9, 2007 to Klofta, et al.; U.S. Pat. No. 7,172,667, entitled "System and method for incorporating graphics into absorbent articles" issued on Feb. 6, 2007 to Vergona; U.S. Pat. No. 7,178,571, entitled "System and method for incorporating graphics into absorbent articles" issued on Feb. 20, 2007 to Vergona; U.S. Pat. No. 7,306,764, entitled "Wetness indicator" issued on Dec. 11, 2007 to Mody; and U.S. Pat. No. 7,332,642, entitled "Disposable absorbent articles having printed wetness indicators" issued on Feb. 19, 2008 to Liu, each of which is incorporated herein by reference.

The absorbent article 300 can be configured such that part, or parts, or all of the primary visual fullness indicator 330 is visible from outside of the absorbent article 300 when the absorbent article 300 is worn by a wearer. As a result, at least some of the subsequent visual state of the primary visual fullness indicator 330 will be visible from outside of the absorbent article 300.

The portion 308 of the absorbent article 300 also includes a first secondary visual wetness indicator 340, a second secondary visual wetness indicator 350, and a third secondary visual wetness indicator 360. A secondary indicator is considered secondary with respect to a primary indicator because it can begin to change states after a primary indicator begins to change states. In alternate embodiments, the portion 308 can only include one of the secondary visual wetness indicators 340, 350, and 360, or the portion 308 can only include any two of the secondary visual wetness indicators 340, 350, and 360, or the portion 308 can include additional secondary visual wetness indicators.

Each of the secondary visual wetness indicators 340, 350, and 360 is spaced apart from the primary visual fullness indicator 330. In various embodiments, one or more parts of a secondary visual wetness indicator can be in contact with one or more parts of a primary visual fullness indicator. The first and second secondary visual wetness indicators 340 and 350 are each spaced apart from a side of the primary visual fullness indicator 330. The third secondary visual wetness indicator 360 is spaced apart from an outboard from the outboard end 333 of the primary visual fullness indicator 330. The third secondary visual wetness indicator 360 is disposed in line with the primary visual fullness indicator 330. In an alternate embodiment, the third secondary visual wetness indicator 360 can be disposed out of line with the primary visual fullness indicator 330.

Each of the secondary visual wetness indicators 340, 350, and 360 is spaced apart from each other. In some embodiments, one or more parts of a secondary visual wetness indicator can be in contact with one or more parts of another secondary visual wetness indicator.

Each of the secondary visual wetness indicators 340, 350, and 360 is disposed proximate to the primary visual fullness indicator 330. This proximity allows a primary visual indicating signal from the primary indicator and a secondary visual indicating signal from a secondary indicator to be viewed together, so the fullness of the article is easy to understand, as described further below. Since the primary and secondary signals are understood together, the primary visual fullness indicator 330 and one or more of the secondary visual wetness indicators 340, 350, and 360, together can be considered a visual fullness indicating system.

Each of the secondary visual wetness indicators 340, 350, and 360 is disposed proximate to the outboard end 333 of the primary visual fullness indicator 330. In some embodiments, a secondary visual wetness indicator can be disposed proximate to another part of a primary visual fullness indicator.

Each of the secondary visual wetness indicators 340, 350, and 360 has an overall indicator length measured along the indicator from its inboard end to its outboard end. The secondary visual wetness indicator 340 includes an inboard end 342 and an outboard end 343. The secondary visual wetness indicator 350 includes an inboard end 352 and an outboard end 353. The secondary visual wetness indicator 360 includes an inboard end 362 and an outboard end 363.

Each of the secondary visual wetness indicators 340, 350, and 360 has an overall indicator length that is less than an overall indicator length of the primary visual fullness indicator 330. In various embodiments, a secondary visual wetness indicator can have an overall length that is the same as or greater than an overall indicator length of the primary visual fullness indicator. Each of the secondary visual wetness indicators 340, 350, and 360 has the same overall indicator length. In some embodiments, secondary visual wetness indicators can have differing overall lengths.

Each of the secondary visual wetness indicators 340, 350, and 360 has an overall shape that is substantially elongated and substantially rectangular. Each of the secondary visual wetness 340, 350, and 360 indicators has a substantially uniform width along its entire overall indicator length. Each of the secondary visual wetness indicators 340, 350, and 360 includes one visual fullness indicating area. Each of the secondary visual wetness indicators 340, 350, and 360 is in continuous fluid communication with an absorbent core of the absorbent article 300 along its entire overall indicator length.

The inboard end of a secondary visual wetness indicator is disposed outboard from the inboard end of a primary visual fullness indicator. As a result, a secondary indicator can begin to change states after a primary indicator begins to change states, as explained in connection with the embodiments of FIGS. 3B-3G.

The inboard end 342 of the first secondary visual wetness indicator 340 is disposed outboard from the inboard end 332 of the primary visual fullness indicator 330 and inboard to the outboard end 333 of the primary visual fullness indicator 330. The outboard end 343 of the first secondary visual wetness indicator 340 is disposed at about the same outboard distance as the outboard end 333 of the primary visual fullness indicator 330. In an alternate embodiment, the outboard end 343 of the first secondary visual wetness indicator 340 can be disposed inboard to the outboard end 333 of the primary visual fullness indicator 330.

The inboard end 352 of the second secondary visual wetness indicator 350 is disposed outboard from the inboard end 332 of the primary visual fullness indicator 330 and inboard to the outboard end 333 of the primary visual fullness indicator 330. The inboard end 352 of the second secondary visual wetness indicator 350 is also disposed outboard from the inboard end 342 of the first secondary visual wetness indicator 340 and inboard to the outboard end 343 of the first secondary visual wetness indicator 340.

The outboard end 353 of the second secondary visual wetness indicator 350 is disposed outboard from the outboard end 333 of the primary visual fullness indicator 330 and outboard from the outboard end 343 of the first secondary visual wetness indicator 340. In an alternate embodiment, the outboard end 353 of the second secondary visual wetness indicator 350 can be disposed inboard to the outboard end 333 of the primary visual fullness indicator 330 and/or inboard to the outboard end 343 of the first secondary visual wetness indicator 340.

The inboard end 362 of the third secondary visual wetness indicator 360 is disposed outboard from the outboard end 333 of the primary visual fullness indicator 330, outboard from the outboard end 343 of the first secondary visual wetness indicator 340, and outboard from the outboard end 353 of the second secondary visual wetness indicator 350. In an alternate embodiment, the inboard end 362 of the third secondary visual wetness indicator 360 can be disposed inboard to the outboard end 343 of the first secondary visual wetness indicator 340, and/or inboard to the outboard end 353 of the second secondary visual wetness indicator 350.

Each of the secondary visual wetness indicators 340, 350, and 360 is configured to change from one or more initial visual states to one or more subsequent visual states when indicating the presence of a liquid bodily exudate. A secondary visual wetness indicator can be configured to have one or more subsequent visual states that can be similar to, the same as, or different from the subsequent visual state of the primary visual fullness indicator. A secondary visual wetness indicator can be configured to have one or more subsequent visual states that can be similar to, the same as, or different from the subsequent visual state of another secondary visual wetness indicator.

The absorbent article 300 can be configured such that part, or parts, or all of each of the secondary visual wetness indicators 340, 350, and 360 is visible from outside of the absorbent article 300 when the absorbent article 300 is worn by a wearer. As a result, at least some of the subsequent visual states of each of the secondary visual wetness indicators 340, 350, and 360 will be visible from outside of the absorbent article 300.

The primary visual fullness indicator 330 and the secondary visual wetness indicators 340, 350, and 360 can be configured to change visual states progressively and in sequence, as illustrated with FIGS. 3B-3G. First, the primary visual fullness indicator 330 can begin to change from an initial visual state to a subsequent visual state when indicating the presence of a liquid bodily exudate to a first extent in an absorbent core of the absorbent article 300. Second, the first secondary visual wetness indicator 340 can begin to change from an initial visual state to a subsequent visual state when indicating the presence of a liquid bodily exudate to a second extent in the absorbent core of the absorbent article 300. Third, the second secondary visual wetness indicator 350 can begin to change from an initial visual state to a subsequent visual state when indicating the presence of a liquid bodily exudate to a third extent in the absorbent core of the absorbent article 300. Fourth, the third secondary visual wetness indicator 360 can begin to change from an initial visual state to a subsequent visual state when indicating the presence of a liquid bodily exudate to a fourth extent in the absorbent core of the absorbent article 300. The partial or complete absence or presence of the subsequent visual states in the indicators 330, 340, 350, and 360 can indicate the fullness of the absorbent article 300.

As a primary visual fullness indicator changes visual states it provides a primary indicating signal. As a secondary visual wetness indicator changes visual states it provides a secondary indicating signal that is separate from and in addition to the primary indicating signal. This combination of a primary indicating signal and a secondary indicating signal is easy to understand, when taken together. Thus, the combination of a primary visual fullness indicator and one or more secondary visual wetness indicators can help provide certainty about the fullness of an absorbent article. In the embodiment of FIG. 3A, the combination of the primary visual fullness indicator 330 and each of the secondary visual wetness indicators 340, 350, and 360, can help provide certainty about the fullness of an absorbent article 300.

By knowing the fullness of an absorbent article, the absorbent article can be changed after a wearer has appropriately utilized its capacity and/or before it is likely to leak. Throughout the present disclosure, the term "capacity" is used to indicate the capacity of the absorbent core alone and does not include the absorbency of other components or structures, such as acquisition or distribution layers. The benefits of the combination of a primary visual fullness indicator and a secondary visual wetness indicator are similarly provided in the embodiments of FIGS. 3B-3G, as described below.

FIGS. 3B-3G illustrate the primary visual fullness indicator 330 and the secondary visual wetness indicators 340, 350, and 360 of the embodiment of FIG. 3A in various states of indication, wherein the indicators change visual states progressively and in sequence in the presence of a liquid bodily exudate to indicate the fullness of the absorbent article 300. In FIGS. 3B-3G, subsequent visual states are illustrated with hatch patterns.

Figure 3B:
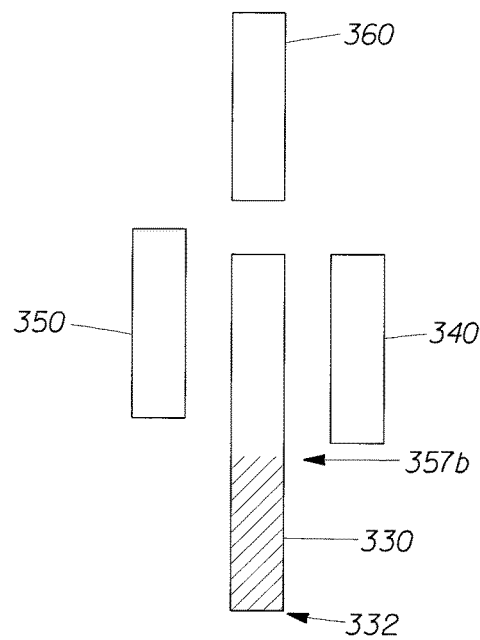
FIG. 3B illustrates a subsequent state of indication for the indicators of FIG. 3A, according to embodiments of the present disclosure.

FIG. 3B illustrates a subsequent state of indication for the indicators of FIG. 3A, wherein part of the primary visual fullness indicator 330 has changed from an initial visual state to a subsequent visual state, to indicate the fullness of the absorbent article 300. In FIG. 3B, a liquid bodily exudate has passed through a portion of the absorbent core of the absorbent article 300 in sufficient concentration to cause a change in visual state from the inboard end 332 up through part of the of the primary visual fullness indicator 330 to a wet edge 357B.

Throughout the present disclosure, a wet edge refers to a boundary along a visual wetness indicator of an absorbent article, wherein the boundary indicates an extent of the presence of a liquid bodily exudate. On the inboard side of the wet edge, the visual wetness indicator has experienced the presence of a liquid bodily exudate at a concentration that is sufficient to cause the visual wetness indicator to change visual states. On the outboard side of the wet edge, the visual wetness indicator has not yet experienced the presence of a liquid bodily exudate at a concentration that is sufficient to cause the visual wetness indicator to change visual states.

Figure 3C:
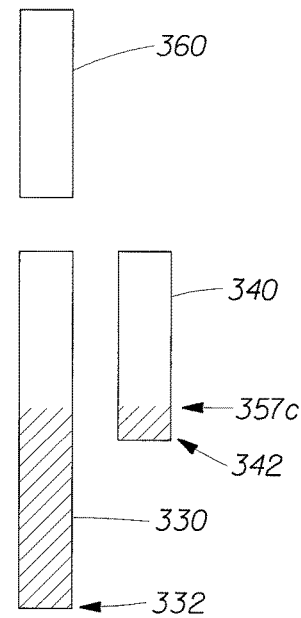
FIG. 3C illustrates a subsequent state of indication for the indicators of FIG. 3B, according to embodiments of the present disclosure.

FIG. 3C illustrates a subsequent state of indication for the indicators of FIG. 3B, wherein part of the primary visual fullness indicator 330 has changed from an initial visual state to a subsequent visual state, and part of the first secondary visual wetness indicator 340 has changed from an initial visual state to a subsequent visual state to indicate the fullness of the absorbent article 300. In FIG. 3C, a liquid bodily exudate has passed through a portion of the absorbent core of the absorbent article 300 in sufficient concentration to cause a change in visual state from the inboard end 332 up through part of the of the primary visual fullness indicator 330 and from the inboard end 342 up through part of the first secondary visual wetness indicator 340 to a wet edge 357C.

Figure 3D:
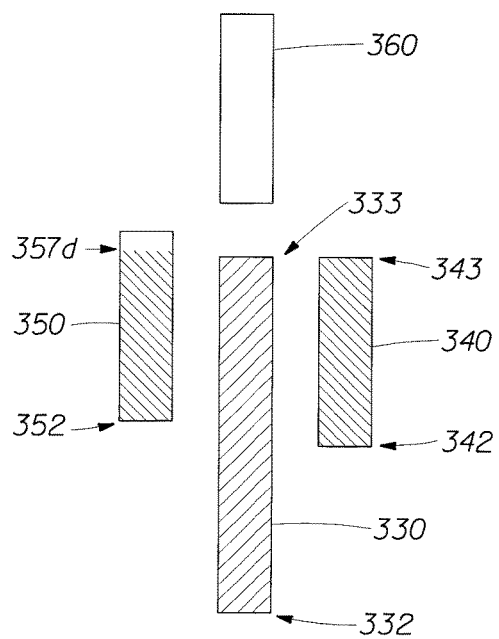
FIG. 3D illustrates a subsequent state of indication for the indicators of FIG. 3C, according to embodiments of the present disclosure.

FIG. 3D illustrates a subsequent state of indication for the indicators of FIG. 3C, wherein all of the primary visual fullness indicator 330 has changed from an initial visual state to a subsequent visual state, all of the first secondary visual wetness indicator 340 has changed from an initial visual state to a subsequent visual state, and part of the second secondary visual wetness indicator 350 has changed from an initial visual state to a subsequent visual state, to indicate the fullness of the absorbent article 300. In FIG. 3D, a liquid bodily exudate has passed through a portion of the absorbent core of the absorbent article 300 in sufficient concentration to cause a change in visual state from the inboard end 342 up through all of the first secondary visual wetness indicator 340 to the outboard end 343, and from the inboard end 352 up through part of the second secondary visual wetness indicator 350, to a wet edge 357D.

Figure 3E:
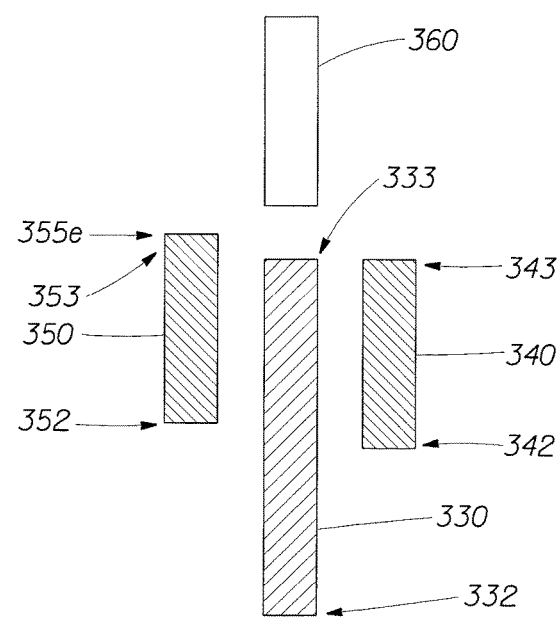
FIG. 3E illustrates a subsequent state of indication for the indicators of FIG. 3D, according to embodiments of the present disclosure.

FIG. 3E illustrates a subsequent state of indication for the indicators of FIG. 3D, wherein all of the primary visual fullness indicator 330 has changed from an initial visual state to a subsequent visual state, all of the first secondary visual wetness indicator 340 has changed from an initial visual state to a subsequent visual state, and all of the second secondary visual wetness indicator 350 has changed from an initial visual state to a subsequent visual state, to indicate the fullness of the absorbent article 300. In FIG. 3E, a liquid bodily exudate has passed through a portion of the absorbent core of the absorbent article 300 in sufficient concentration to cause a change in visual state from the inboard end 332 up through all of the of the primary visual fullness indicator 330 to the outboard end 333, from the inboard end 342 up through all of the first secondary visual wetness indicator 340 to the outboard end 343, and from the inboard end 352 up through all of the second secondary visual wetness indicator 350 to a wet edge 357E at the outboard end 353.

Figure 3F:
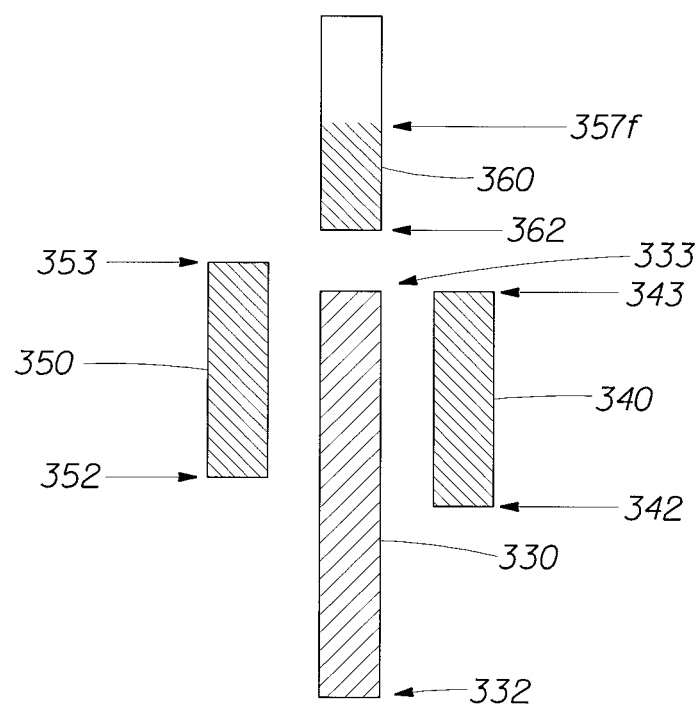
FIG. 3F illustrates a subsequent state of indication for the indicators of FIG. 3E, according to embodiments of the present disclosure.

FIG. 3F illustrates a subsequent state of indication for the indicators of FIG. 3E, wherein all of the primary visual fullness indicator 330 has changed from an initial visual state to a subsequent visual state, all of the first secondary visual wetness indicator 340 has changed from an initial visual state to a subsequent visual state, all of the second secondary visual wetness indicator 350 has changed from an initial visual state to a subsequent visual state, and part of the third secondary visual wetness indicator 360 has changed from an initial visual state to a subsequent visual state, to indicate the fullness of the absorbent article 300. In FIG. 3F, a liquid bodily exudate has passed through a portion of the absorbent core of the absorbent article 300 in sufficient concentration to cause a change in visual state from the inboard end 332 up through all of the of the primary visual fullness indicator 330 to the outboard end 333, from the inboard end 342 up through all of the first secondary visual wetness indicator 340 to the outboard end 343, from the inboard end 352 up through all of the second secondary visual wetness indicator 350 to the outboard end 353, and from the inboard end 362 up through part of the third secondary visual wetness indicator 360 to a wet edge 357F.

Figure 3G:
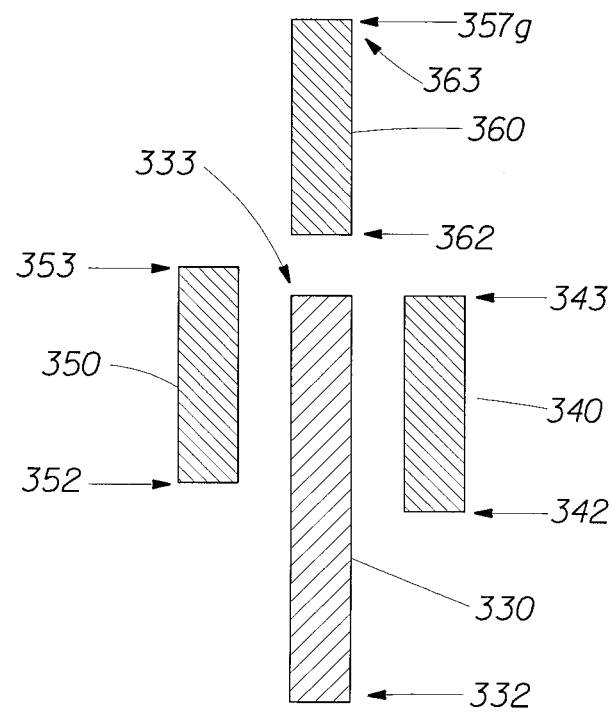
FIG. 3G illustrates a subsequent state of indication for the indicators of FIG. 3F, according to embodiments of the present disclosure.

FIG. 3G illustrates a subsequent state of indication for the indicators of FIG. 3F, wherein all of the primary visual fullness indicator 330 has changed from an initial visual state to a subsequent visual state, all of the first secondary visual wetness indicator 340 has changed from an initial visual state to a subsequent visual state, all of the second secondary visual wetness indicator 350 has changed from an initial visual state to a subsequent visual state, and all of the third secondary visual wetness indicator 360 has changed from an initial visual state to a subsequent visual state, to indicate the fullness of the absorbent article 300. In FIG. 3F, a liquid bodily exudate has passed through a portion of the absorbent core of the absorbent article 300 in sufficient concentration to cause a change in visual state from the inboard end 332 up through all of the of the primary visual fullness indicator 330 to the outboard end 333, from the inboard end 342 up through all of the first secondary visual wetness indicator 340 to the outboard end 343, from the inboard end 352 up through all of the second secondary visual wetness indicator 350 to the outboard end 353, and from the inboard end 362 up through all of the third secondary visual wetness indicator 360 to a wet edge 357F at the outboard end 363.

Together, FIGS. 3B-3G illustrate that the indicators 330, 340, 350, and 360 can change visual states progressively and in sequence in the presence of a liquid bodily exudate to indicate the degree to which a liquid bodily exudate has filled the absorbent article 300. In addition to indicating fullness, in embodiments of the present disclosure, such changes in visual state in a visual fullness indicating system can also be understood as a signal that indicates the remaining absorbent capacity of an absorbent article and/or as a signal that indicates the risk that an absorbent article may leak.

An appropriate particular location and orientation as well as specific dimensions and other physical characteristics for an indicator of the present disclosure can be selected in order for an indicator to provide visual state change signals that indicate the degree of fullness, the remaining capacity, and/or the leakage risk for a particular absorbent article. In various embodiments, the absorbent article can also include indicia correlating the visual state change signals with fullness, capacity, and/or leakage risk.

The locations of a primary visual fullness indicator and a secondary visual wetness indicator enable the user to understand when the article should be changed. A secondary visual wetness indicator can be positioned relative to the primary visual fullness indicator such that a user can understand that if the article is left on for a further period of time, the chance of the article leaking is increased. An absorbent article becomes more likely to leak when the absorbent core is nearing full utilization, e.g., most of its capacity has been used. As an absorbent article is worn, the wearer exudes bodily exudates (esp. urine) from a particular location on their body. The bodily exudates are absorbed by the absorbent core. The core tends to fill initially near the location the user loads the product and then begins to fill farther and farther from the loading point as the portion near the loading location begins to become saturated. As this occurs, the primary visual fullness indicator changes visual state to indicate the presence of a bodily exudate in that portion of the core. As the bodily exudate spreads through the core, the primary visual fullness indicator progressively changes visual state along its length.

Once the core is nearly full (most of the capacity is utilized), the absorbent core may no longer be capable of storing additional insults of bodily exudates. At this point, the risk of exudates leaking from the article increases. One or more secondary visual wetness indicators can be located in the article to indicate this additional risk of leakage, which can prompt the user to change the product.

A secondary visual wetness indicator can be located in an absorbent article in light of the following principles. First, an inboard end of a secondary visual wetness indicator can be located in a portion of the article where exudates are unlikely be stored in typical use of the article. Such locations can include: (a) a portion of an absorbent core that is remote from an acquisition or distribution layer; (b) a portion of an absorbent core that is remote from the source of the bodily exudate; and (c) a portion of an absorbent core having a relatively low storage capacity. Second, an inboard end of a secondary visual wetness indicator can be located in a portion of the article where there is "low saturation" (e.g., a portion of the core which, in typical use, does not become as highly saturated as portions of the core adjacent to a loading zone of the article).

Further, in some embodiments, instructions for the absorbent article can explain the correlation between the visual state change signals and fullness, capacity, and/or leakage risk. For example, such instructions can be provided on packaging for the absorbent article or on printed material accompanying the absorbent article. Still further, the correlation between the visual state change signals and fullness, capacity, and/or leakage risk can be communicated through various advertising media.

For each visual fullness indicator of the present disclosure, the location of the inboard end and the outboard end can be selected to provide visual signals that indicate the degree of fullness, the remaining capacity, and/or the leakage risk for the absorbent article in which the indicator is included.

As a first example, in various embodiments, an inboard end of a primary visual fullness indicator can be disposed at a particular location, such that, a change in visual state at that inboard end (i.e. a wet edge proximate to that inboard end) indicates that the absorbent article has: (a) a fullness of about 25%, 30%, 35%, 40%, 45%, 50%, 55%, 60%, 65%, 70%, 75%, 80%, 85%, or any integer of percentage between any of these values, or within any range using any of these values; (b) a remaining capacity of about 75%, 70%, 65%, 60%, 55%, 50%, 45%, 40%, 35%, 30%, 25%, 20%, 15%, or any integer of percentage between any of these values, or within any range using any of these values; and/or (c) a leakage risk of >0%, 5%, 10%, 15%, 20%, 25%, 30%, 35%, 40%, 45%, 50%, 55%, 60%, 65%, 70%, 75%, 80%, 85%, or any integer of percentage between any of these values, or within any range using any of these values. As used herein, the term "leakage risk" refers to the probability of a liquid bodily exudate leaking out of a diaper, while the diaper is being properly worn by a wearer of appropriate size, with such probability being measured in a sufficient number of diapers being used by a sufficient number of wearers of appropriate size. For example, at least 100 users should use at least five days worth of diapers to determine the probability of a diaper leaking.

An inboard end of a primary visual fullness indicator can be disposed in an absorbent article at any of the following locations: 80 mm, 70 mm, 60 mm, 50 mm, 40 mm, 30 mm, 20 mm, 10 mm, or 5 mm inboard to an outer edge of an acquisition layer; at an outer edge of an acquisition layer; 80 mm, 70 mm, 60 mm, 50 mm, 40 mm, 35 mm, 30 mm, 25 mm, 20 mm, 15 mm, 10 mm, or 5 mm inboard to an outer edge of a distribution layer; at an outer edge of a distribution layer; 140 mm, 130 mm, 120 mm, 110 mm, 100 mm, 90 mm, 80 mm, 70 mm, 60 mm, 50 mm, 40 mm, 30 mm, 20 mm, 10 mm, or 5 mm inboard to an outer edge of an absorbent core; or at an outer edge of an absorbent core. An inboard end of a primary visual fullness indicator can also be disposed in an absorbent article at any integer of mm between any of these values or within any range using any of these values.

As a second example, in various embodiments, an outboard end of a primary visual fullness indicator can be disposed at a particular location, such that, a change in visual state at that outboard end (i.e. a wet edge proximate to that outboard end) indicates that the absorbent article has: (a) a fullness of 30%, 35%, 40%, 45%, 50%, 55%, 60%, 65%, 70%, 75%, 80%, 85%, 90%, or any integer of percentage between any of these values, or within any range using any of these values; (b) a remaining capacity of 70%, 65%, 60%, 55%, 50%, 45%, 40%, 35%, 30%, 25%, 20%, 15%, 10%, or any integer of percentage between any of these values, or within any range using any of these values; and/or (c) a leakage risk of 30%, 35%, 40%, 45%, 50%, 55%, 60%, 65%, 70%, 75%, 80%, 85%, 90%, or any integer of percentage between any of these values, or within any range using any of these values.

An outboard end of a primary visual fullness indicator can be disposed in an absorbent article at any of the following locations: 70 mm, 60 mm, 50 mm, 40 mm, 30 mm, 20 mm, 10 mm, or 5 mm inboard to an outer edge of an acquisition layer; at an outer edge of an acquisition layer; 5 mm or 10 mm outboard from an outer edge of an acquisition layer; 70 mm, 60 mm, 50 mm, 40 mm, 30 mm, 25 mm, 20 mm, 15 mm, 10 mm, or 5 mm inboard to an outer edge of a distribution layer; at an outer edge of a distribution layer; 5 mm or 10 mm outboard from an outer edge of a distribution layer; 130 mm, 120 mm, 110 mm, 100 mm, 90 mm, 80 mm, 70 mm, 60 mm, 50 mm, 40 mm, 30 mm, 20 mm, 10 mm, or 5 mm inboard to an outer edge of an absorbent core; at an outer edge of an absorbent core; or 5 mm or 10 mm outboard from an outer edge of an absorbent core. An outboard end of a primary visual fullness indicator can also be disposed in an absorbent article at any integer of mm between any of these values, or within any range using any of these values.

As a third example, in various embodiments, an inboard end of a secondary visual wetness indicator can be disposed at a particular location, such that, a change in visual state at that inboard end (i.e. a wet edge proximate to that inboard end) indicates that the absorbent article has: (a) a fullness of 50%, 55%, 60%, 65%, 70%, 75%, 80%, 85%, 90%, 95% or any integer of percentage between any of these values, or within any range using any of these values; (b) a remaining capacity of 50%, 45%, 40%, 35%, 30%, 25%, 20%, 15%, 10%, 5%, or any integer of percentage between any of these values, or within any range using any of these values; and/or (c) a leakage risk of 10%, 20%, 30%, 40%, 50%, 60%, 70%, 80%, 90%, or any integer of percentage between any of these values, or within any range using any of these values A change in visual state at an inboard end of a secondary visual wetness indicator may indicate a fullness that is less than, or equal to, or greater than a fullness indicated by a change in visual state at an outboard end of a primary visual fullness indicator. A change in visual state at an inboard end of a secondary visual wetness indicator may indicate a remaining capacity that is greater than, or equal to, or less than a remaining capacity indicated by a change in visual state at an outboard end of a primary visual fullness indicator. A change in visual state at an inboard end of a secondary visual wetness indicator may indicate a leakage risk that is greater than, or equal to, or less than a leakage risk indicated by a change in visual state at an outboard end of a primary visual fullness indicator.

As a fourth example, in various embodiments, an outboard end of a secondary visual wetness indicator can be disposed at a particular location, such that, a change in visual state at that outboard end (i.e. a wet edge proximate to that outboard end) indicates that the absorbent article has: (a) a fullness of 55%, 60%, 65%, 70%, 75%, 80%, 85%, 90%, 95%, about 100%, or any integer of percentage between any of these values, or within any range using any of these values; (b) a remaining capacity of 45%, 40%, 35%, 30%, 25%, 20%, 15%, 10%, 5%, about 0%, or any integer of percentage between any of these values, or within any range using any of these values; and/or (c) a leakage risk of 20%, 30%, 40%, 50%, 60%, 70%, 80%, 90%, about 100%, or any integer of percentage between any of these values, or within any range using any of these values.

It is contemplated that any of the four exemplary embodiments described above can be applied in any workable combination to any relevant embodiment of the present disclosure. A visual fullness indicator can also be located in an absorbent article as described in connection with the embodiment of FIG. 4.

Figure 4:
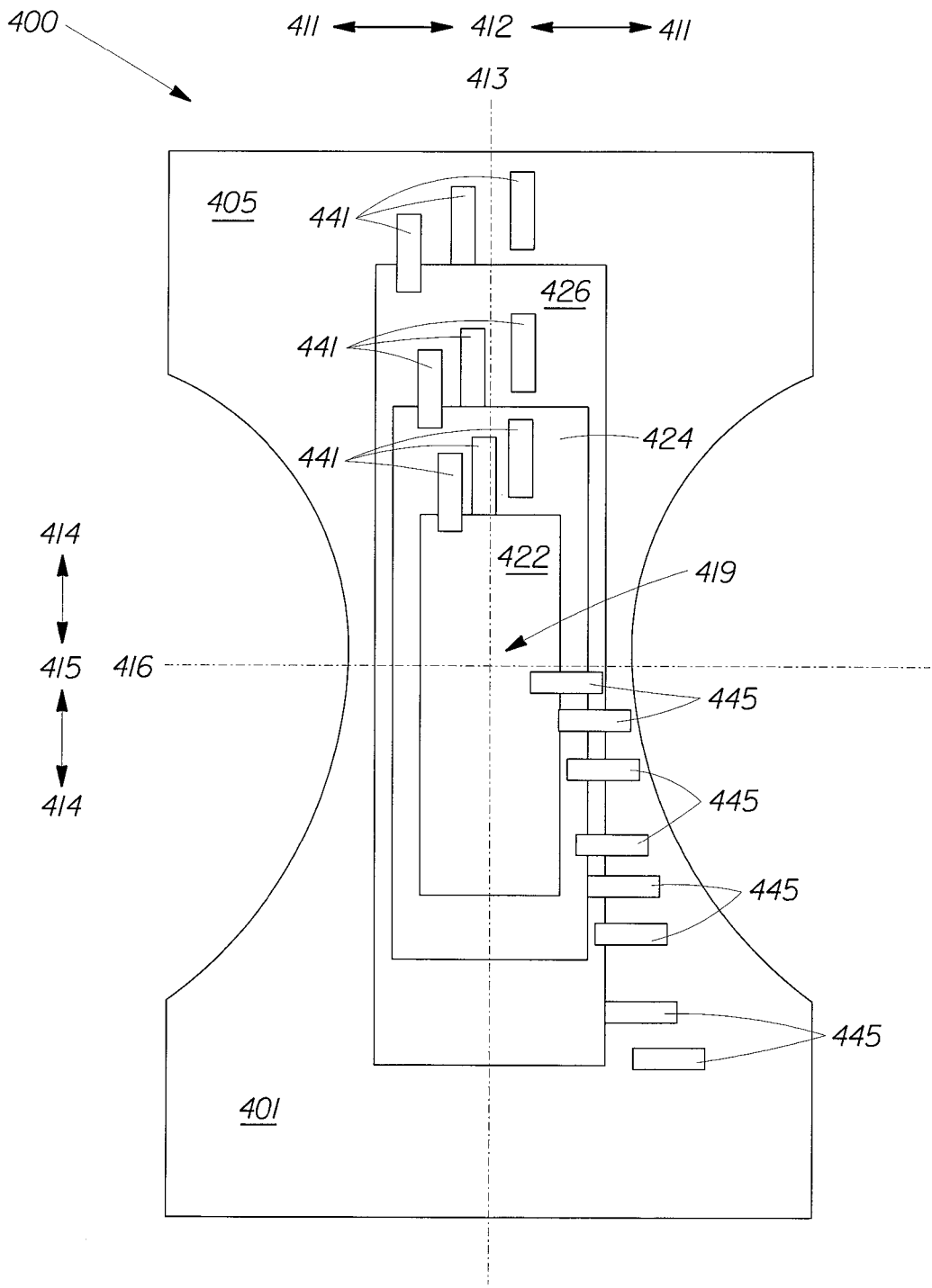
FIG. 4 illustrates a pant-type disposable wearable absorbent article with a number of secondary visual wetness indicators, according to embodiments of the present disclosure.

FIG. 4 illustrates a plan view of an inside of a pant-type disposable wearable absorbent article 400 laid out flat. The locations of the elements in the embodiment of FIG. 4 can also apply to embodiments of front-fastenable disposable wearable absorbent articles, as will be understood by one of ordinary skill in the art. The disposable wearable absorbent article 400 includes a front 401, a back 405, an acquisition layer 422, a distribution layer 424, and an absorbent core 426. The disposable wearable absorbent article 400 also includes a longitudinal centerline 413 and a lateral centerline 416, which provide lines of reference for relative directions of laterally outboard 411, laterally inboard 412, longitudinally outboard 414, and longitudinally inboard 415.

The disposable wearable absorbent article 400 includes a number of secondary visual wetness indicators 441 in the front 401 and a number of secondary visual wetness indicators 445 in the back 405 in various exemplary locations and orientations. Any of the secondary visual wetness indicators of the present disclosure can be located and/or orientated as any of the secondary visual wetness indicators 441 or 445 are located and/or oriented in FIG. 4.

The embodiment of FIG. 4 illustrates the various secondary visual wetness indicators 441 with an inboard end disposed: longitudinally inboard to a longitudinally outboard edge of the acquisition layer 422, at the longitudinally outboard edge of the acquisition layer 422, and longitudinally outboard from the longitudinally outboard edge of the acquisition layer 422. An inboard end of a secondary visual wetness indicator can be disposed in an absorbent article at any of the following locations: 75 mm, 70 mm, 60 mm, 50 mm, 40 mm, 30 mm, 20 mm, 10 mm, or 5 mm inboard to an outer edge of an acquisition layer; at an outer edge of an acquisition layer; or 5 mm, 10 mm, or 20 mm outboard from an outer edge of an acquisition layer. An inboard end of a secondary visual wetness indicator can also be disposed in an absorbent article at any integer of mm between any of these values, or within any range using any of these values.

The embodiment of FIG. 4 also illustrates the various secondary visual wetness indicators 441 with an inboard end disposed: longitudinally inboard to a longitudinally outboard edge of the distribution layer 424, at the longitudinally outboard edge of the distribution layer 424, and longitudinally outboard from the longitudinally outboard edge of the acquisition layer 424. An inboard end of a secondary visual wetness indicator can be disposed in an absorbent article at any of the following locations: 75 mm, 70 mm, 660 mm, 50 mm, 40 mm, 30 mm, 25 mm, 20 mm, 15 mm, 10 mm, or 5 mm inboard to an outer edge of a distribution layer; at an outer edge of a distribution layer; or 5 mm, 10 mm, or 20 mm outboard from an outer edge of a distribution layer. An inboard end of a secondary visual wetness indicator can also be disposed in an absorbent article at any integer of mm between any of these values, or within any range using any of these values.

The embodiment of FIG. 4 further illustrates the various secondary visual wetness indicators 441 with an inboard end disposed: longitudinally inboard to a longitudinally outboard edge of the absorbent core 426, at the longitudinally outboard edge of the absorbent core 426, and longitudinally outboard from the longitudinally outboard edge of the absorbent core 426. An inboard end of a secondary visual wetness indicator can be disposed in an absorbent article at any of the following locations: 120 mm, 110 mm, 100 mm, 90 mm, 80 mm, 70 mm, 60 mm, 50 mm, 40 mm, 30 mm, 20 mm, or 10 mm inboard to an outer edge of an absorbent core; at an outer edge of an absorbent core; or 5 mm, 10 mm, or 20 mm outboard from an outer edge of an absorbent core. An inboard end of a secondary visual wetness indicator can also be disposed in an absorbent article at any integer of mm between any of these values, or within any range using any of these values.

In various embodiments, a secondary visual wetness indicator disposed in the back of an article can have an inboard end disposed with respect to a longitudinally outboard edge of an absorbent core disposed in the front of the article. In this way, the secondary visual indicating signal can be configured with respect to a point in the front/center of the article, where liquid bodily exudates are provided to the article by the wearer. As examples, a secondary visual wetness indicators can be disposed in the back of an article with an inboard end of the indicator disposed 275 mm, 270 mm, 260 mm, 250 mm, 240 mm, 230 mm, 220 mm, 210 mm, 200 mm, 190 mm, 180 mm, 170 mm, 160 mm, or 150 mm, from a longitudinally outboard edge of an absorbent core disposed in the front of the article. An inboard end of a secondary visual wetness indicator can also be disposed in an absorbent article at any integer of mm between any of these values, or within any range using any of these values.

An outboard end of a secondary visual wetness indicator can be disposed in an absorbent article at any of the following locations: 50 mm, 40 mm, 30 mm, 20 mm, 10 mm, or 5 mm inboard to an outer edge of an acquisition layer; at an outer edge of an acquisition layer; 5 mm, 10 mm, 20 mm, or 30 mm outboard from an outer edge of an acquisition layer; 50 mm, 40 mm, 30 mm, 25 mm, 20 mm, 15 mm, 10 mm, or 5 mm inboard to an outer edge of a distribution layer; at an outer edge of a distribution layer; 5 mm, 10 mm, 20 mm, or 30 mm outboard from an outer edge of a distribution layer; 110 mm, 100 mm, 90 mm, 80 mm, 70 mm, 60 mm, 50 mm, 40 mm, 30 mm, 20 mm, or 10 mm inboard to an outer edge of an absorbent core; at an outer edge of an absorbent core; or 5 mm, 10 mm, 20 mm, or 30 mm outboard from an outer edge of an absorbent core. An outboard end of a secondary visual wetness indicator can also be disposed in an absorbent article at any integer of mm between any of these values, or within any range using any of these values.

Any of the secondary visual wetness indicators 441 can be disposed on the longitudinal centerline 413, proximate to the longitudinal centerline 413, laterally offset from the longitudinal centerline 413, or at some other lateral location. These locations and orientations for the secondary visual wetness indicators 441 disposed in the front 401 can be similarly applied to secondary visual wetness indicators disposed in the back 405.

The embodiment of FIG. 4 illustrates the various secondary visual wetness indicators 445 with an inboard end disposed: laterally inboard to a laterally outboard edge of the acquisition layer 422, at the laterally outboard edge of the acquisition layer 422, laterally outboard from the laterally outboard edge of the acquisition layer 422, laterally inboard to a laterally outboard edge of the distribution layer 424, at the laterally outboard edge of the distribution layer 424, laterally outboard from the laterally outboard edge of the acquisition layer 424, laterally inboard to a laterally outboard edge of the absorbent core 426, at the laterally outboard edge of the absorbent core 426, or laterally outboard from the laterally outboard edge of the absorbent core 426. Any of the secondary visual wetness indicators 445 can be disposed on the lateral centerline 416, proximate to the lateral centerline 416, longitudinally offset from the lateral centerline 416, or at some other longitudinal location. These locations and orientations for the secondary visual wetness indicators 445 disposed in the front 405 can be similarly applied to secondary visual wetness indicators disposed in the front 401.

It is contemplated that any of the secondary visual wetness indicators 441 and 445 can be applied in any workable combination to any relevant embodiment of the present disclosure.

The location and orientation of a secondary visual wetness indicator in a disposable wearable absorbent article can be selected in various ways. Since a secondary visual wetness indicator can provide a secondary indicating signal indicating a leakage risk, a secondary visual wetness indicator can be located in a region of an article where the absorbent core will become saturated at a time relatively close to, but before, the time at which the article is likely to leak. Typically, manufacturers design absorbent articles to reduce the amount of unused absorbent material in order to make the articles affordable to the consumer. Therefore, a secondary visual wetness indicator can be located in a region of an article significantly closer to an outboard edge of the absorbent core than to a region expected to receive the majority of urine insults.

In some embodiments, a secondary visual wetness indicator can be located in an absorbent article based on the location, or profile, of the absorbent capacity of an absorbent core of the article. The Teabag Centrifuge Capacity test, or TCC test, (described in U.S. Pat. No. 6,278,037) can be used to determine the capacity of an absorbent core, a portion of an absorbent core, or an absorbent core material. A portion of an absorbent core can be subjected to the TCC test. For example, a core can be cut parallel to a lateral centerline of an absorbent article at a location corresponding to an inboard edge of a secondary visual wetness indicator and subsequently subjected to the TCC test.

If an absorbent article includes more than one secondary visual wetness indicator and each secondary visual wetness indicator is located at a different longitudinal location in the article, then one separately evaluates the capacity of the portion of the core longitudinally outboard from each indicator. For example, a set of samples is evaluated for capacity outboard a first secondary visual wetness indicator, and then separate sets of samples are evaluated for each additional secondary visual wetness indicator. Further, the method is performed as described in U.S. Pat. No. 6,278,037. Of specific note, given an absorbent core typically weighs more than 0.200 grams, the total capacity and capacity longitudinally outboard of a secondary visual wetness indicator is determined from preparation of multiple teabags. Total capacity of the absorbent core, capacity of the portion longitudinally outboard of a secondary visual wetness indicator, and percent of capacity located longitudinally outboard of the secondary visual wetness indicator are determined as follows.

First, prepare as many teabag samples as required to measure the total capacity and the capacity of the portion longitudinally outboard of a secondary visual wetness indicator. Test them as outlined in U.S. Pat. No. 6,278,037. Test a blank teabag for each individual teabag containing core material. Second, determine the capacity of each portion being evaluated. The capacity of the portion is equal to the sum of all sample teabag weights after centrifuging minus the sum of all blank teabag weights after centrifuging minus the sum of all dry absorbent material weights. Third, calculate the percent of the total capacity that is longitudinally outboard from the secondary visual wetness indicator. This percentage is equal to 100 times the capacity of the absorbent core longitudinally outboard from the secondary visual wetness indicator divided by the total core capacity. Repeat this test for at least three samples and report the results as an average.

A secondary visual wetness indicator can also be located within an absorbent article such that the capacity of a portion of an absorbent core lying outboard from an inboard edge of the indicator can be less than 20 grams of 0.9% saline solution per the TCC test. In some embodiments, a secondary visual wetness indicator can be located in an absorbent article such that the capacity of a portion of an absorbent core lying outboard from an inboard edge of the indicator can be less than 30 grams, 50 grams, 100 grams of 0.9% saline solution per the TCC test, or any integer of grams between any of these values, or within a range defined by any of the above-mentioned percentages.

Since a secondary visual wetness indicator can provide a visual signal indicating relative leakage risk, a secondary visual wetness indicator can be located in a region of an absorbent article where an absorbent core will become sufficiently saturated to trigger the indicator just prior to loadings at which leakage may be expected. Wetness indicators typically require some minimum amount, Cmin (or minimum concentration), of free or available aqueous fluid in order to trigger the change in visual state of the indicator. In the case of absorbent articles, the fluid is a liquid bodily exudate, such as urine. Many absorbent articles include an absorbent core that will absorb and retain under a moderate pressure (e.g., a pressure expected to be experienced during normal use of the article—such as 0.5 psi) a small amount of fluid that does not provide a sufficient concentration of free fluid, i.e., Cmin, to trigger a wetness indicator in contact with said core. Upon sufficient fluid loading, absorbent cores will typically release free fluid, in significant concentrations, such as Cmin, thereby enabling a wetness indicator in contact with the core to change visual states.

A given core construction will be able to absorb a given amount of fluid prior to yielding Cmin free fluid to a contacting wetness indicator. The amount of fluid absorbed by a core, i.e., loading, prior to Cmin fluid being made available (or "expressed") from the core under a moderate pressure is dependent on its construction. For a given type or ratio of core materials, the higher the Teabag Centrifuge Capacity (TCC) of a core, or portion of a core, generally the higher the core loading may be prior to Cmin free fluid availability from the core. Certain core materials hold fluid more tightly—e.g., under greater pressures. For example, superabsorbent polymers as known in the art can hold more fluid, under higher pressures, than airfelt or other cellulosic or foam materials. Therefore, higher concentrations of superabsorbent polymers, or other materials with similar fluid retention-under-pressure behavior, result in higher fluid loadings in cores prior to Cmin free fluid availability. Cmin for many suitable cores and suitable wetness indicators of interest ranges from about 0.2 ml/cm$^2$ to 0.35 ml/cm$^2$. To determine where to place a secondary visual wetness indicator, one can determine the absorbent core saturation as a function of location in used absorbent articles. A suitable method for determining this is described in steps 1-8 of the Method for Locating a Secondary Indicator, by collecting used absorbent articles, harvesting the absorbent cores, and determining the core saturation (in ml of urine held in the core per cm$^2$ of core) as a function of distance from the front edge of the core. Plotting the core saturation on the Y-axis vs. distance from the front edge of the core provides a loading profile, such as the exemplary loading profile shown in FIG. 5A.

Figure 5A:
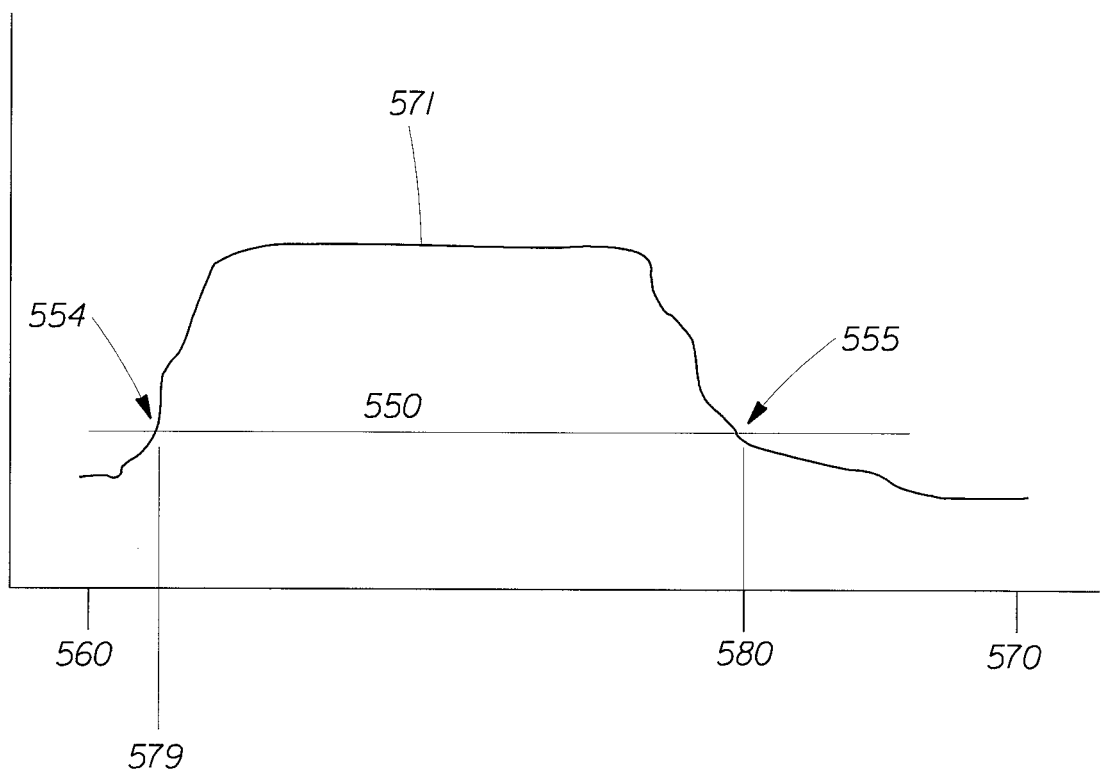
FIG. 5A illustrates an exemplary loading profile for an absorbent core of a disposable wearable absorbent, according to embodiments of the present disclosure.

In FIG. 5A, the horizontal axis represents the longitudinal dimension of the diaper core and the vertical axis represents the concentration of the liquid in the diaper core, in terms of liquid volume per area, as described in the above method. The front edge of the absorbent core is designated 560 and the back edge of the absorbent core is designated 570. The loading profile varies over along the longitudinal dimension of the diaper. Cmin 550 is shown plotted as a horizontal line. The intersections of the loading profile 571 and the Cmin line 550 are designated Front Saturation Threshold Point 554 and Back Saturation Threshold Point 555. Vertical lines are drawn from the intersections point 554 and 555 to the horizontal axis to mark Front Saturation Threshold Location 579 and Back Saturation Threshold Location 580, which represents longitudinal locations along the length of the diaper core. Front and Rear Saturation Threshold Locations 579 and 580 are determined for values of Cmin of 0.20, 0.25, 0.30, and 0.35 ml/cm$^2$.

In preferred embodiments, the inboard end of a secondary visual indicator is located as described below in the Method for Locating a Secondary Indicator.

Method for Locating a Secondary Indicator

Figure 6:
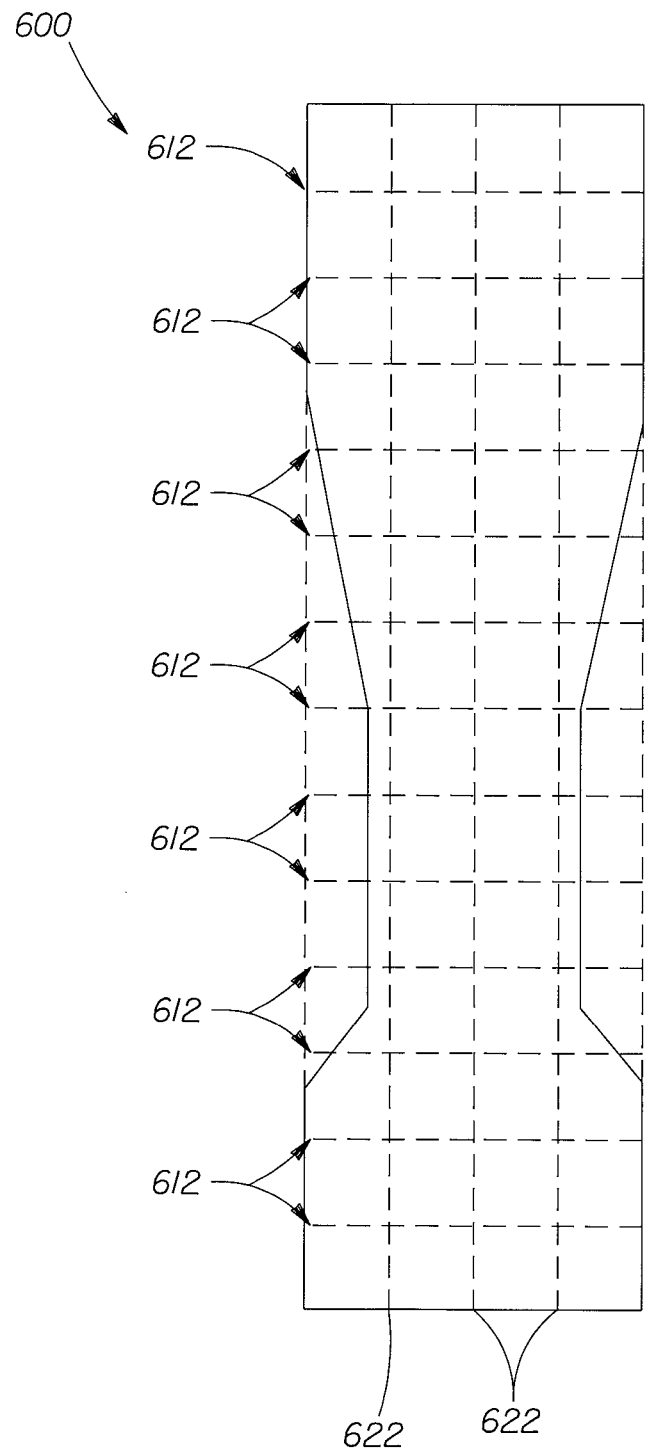
FIG. 6 illustrates an exemplary absorbent core, according to embodiments of the present disclosure.

This method is described in relation to an exemplary embodiment illustrated in FIGS. 6 and 7 and the tables referenced below.

1. As illustrated in FIG. 6, an absorbent core 600 is separated out from an absorbent article and is divided into a number of sections from S1-1 to Sn-n, determined by the size and resolution desired.

2. Divide the absorbent core 600 into sections by making longitudinal cuts 622 and lateral cuts 612. As an example, as shown in FIG. 6, an absorbent core can be divided longitudinally into 14 sections and can be divided laterally into 4 sections. For each section, determine the area, which is defined as A1-1 to An-n. Table 1A, shows exemplary area data for the sections of the sample absorbent core 600.

TABLE 1A

| | SECTION AREAS [cm$^2$] | | | |
|---|---|---|---|---|
| | 1 | 2 | 3 | 4 |
| 1 | 8.4 | 9.0 | 9.0 | 8.4 |
| 2 | 8.4 | 9.0 | 9.0 | 8.4 |
| 3 | 7.9 | 9.0 | 9.0 | 7.9 |
| 4 | 2.6 | 9.0 | 9.0 | 2.6 |
| 5 | 1.5 | 9.0 | 9.0 | 1.5 |
| 6 | 1.5 | 9.0 | 9.0 | 1.5 |
| 7 | 1.5 | 9.0 | 9.0 | 3.5 |
| 8 | 2.6 | 9.0 | 9.0 | 2.6 |
| 9 | 4.7 | 9.0 | 9.0 | 4.7 |
| 10 | 6.8 | 9.0 | 9.0 | 6.8 |
| 11 | 8.3 | 9.0 | 9.0 | 8.3 |
| 12 | 8.4 | 9.0 | 9.0 | 8.4 |
| 13 | 8.4 | 9.0 | 9.0 | 8.4 |
| 14 | 8.4 | 9.0 | 9.0 | 8.4 |

3. For each section of the absorbent core, determine and tabulate the dry weight (weight without loading). The dry weights are defined as the Wdry1-1 to Wdryn-n. This can be done by weighing each section with an appropriate balance having 0.00 grams precision. Repeat this process for at least ten unused articles and take the average.

4. Acquire used absorbent articles from a use test where users used several absorbent articles and data was captured for each article used by each user including data on whether or not the absorbent article leaked. The use test should include absorbent articles used by at least 100 users over a period of at least 5 days.

5. For each used absorbent article, separate the absorbent core from the rest of the article and divide the absorbent core into the number of sections from S1-1 to Sn-n, with the same areas shown in Table 1A.

6. For each section of the absorbent core, determine and tabulate the wet weight (weight loading from bodily exudates). These wet weights are defined as Wwet1-1 to Wwetn-n.

7. For each section of the absorbent core, determine the load by subtracting the dry weight Wdry from the wet weight Wwet. The formula to calculate the load per section is: Wload=Wwet−Wdry. The loads are defined as the Wload1-1 to Wloadn-n. Table 1B shows exemplary load data for the sections of the sample absorbent core 600 (the data is shown in milliliters (ml) since 1 gram of water is about 1 milliliter). Also, determine the load for the entire absorbent core.

TABLE 1B

SECTION LOADS [ml]

|   | 1 | 2 | 3 | 4 |
|---|---|---|---|---|
| 1 | 2.70 | 6.30 | 6.30 | 2.70 |
| 2 | 4.95 | 11.55 | 11.55 | 4.95 |
| 3 | 5.85 | 13.65 | 13.65 | 5.85 |
| 4 | 2.05 | 18.45 | 18.45 | 2.05 |
| 5 | 2.25 | 20.25 | 20.25 | 2.25 |
| 6 | 2.55 | 22.95 | 22.95 | 2.55 |
| 7 | 2.60 | 23.40 | 23.40 | 2.60 |
| 8 | 2.45 | 22.05 | 22.05 | 2.45 |
| 9 | 2.25 | 20.25 | 20.25 | 2.25 |
| 10 | 6.00 | 14.00 | 14.00 | 6.00 |
| 11 | 4.20 | 9.80 | 9.80 | 4.20 |
| 12 | 0.90 | 2.10 | 2.10 | 0.90 |
| 13 | 0.30 | 0.70 | 0.70 | 0.30 |
| 14 | 0.15 | 0.35 | 0.35 | 0.15 |

8. For each section of the absorbent core 600, determine and tabulate the concentration of bodily exudates by dividing the load by the area. The formula to calculate the concentration per section is: C=Wload/A. Table 1C shows exemplary concentration data for the sections of the sample absorbent core 600.

TABLE 1C

SECTION CONCENTRATIONS [ml/cm$^2$]

|   | 1 | 2 | 3 | 4 |
|---|---|---|---|---|
| 1 | 0.32 | 0.70 | 0.70 | 0.32 |
| 2 | 0.59 | 1.28 | 1.28 | 0.59 |
| 3 | 0.74 | 1.52 | 1.52 | 0.74 |
| 4 | 0.78 | 2.05 | 2.05 | 0.78 |
| 5 | 1.50 | 2.25 | 2.25 | 1.50 |
| 6 | 1.70 | 2.55 | 2.55 | 1.70 |
| 7 | 1.73 | 2.60 | 2.60 | 1.73 |
| 8 | 0.96 | 2.45 | 2.45 | 0.96 |
| 9 | 0.48 | 2.25 | 2.25 | 0.48 |
| 10 | 0.88 | 1.56 | 1.56 | 0.88 |
| 11 | 0.50 | 1.09 | 1.09 | 0.50 |
| 12 | 0.11 | 0.23 | 0.23 | 0.11 |
| 13 | 0.04 | 0.08 | 0.08 | 0.04 |
| 14 | 0.02 | 0.04 | 0.04 | 0.02 |

9. In the area in which the secondary indicator is to be located, determine which sections have a concentration of bodily exudates above the minimum concentration Cmin of liquid bodily exudates that will trigger the secondary indicator (Cmin). In the example provided, if the minimum concentration is 0.30 ml/cm$^2$ and the area in which the secondary indicator is to be located corresponds with the sections of column 2, then the sections having a concentration of bodily exudates above Cmin are sections S1-2 to S11-2. Determine and record the length of those sections in relation to a reference point, such as the lateral centerline of the article.

10. Repeat steps 5-9 for all the used absorbent articles acquired in step 4. Table 1D shows exemplary length data for the sections of the sample absorbent core 600. For each of the absorbent articles, tabulate the load for the entire absorbent core (from step 7), correlated with the length (from step 9), and whether or not the article leaked (from step 4). Table 1D shows this data for 27 exemplary absorbent articles.

TABLE 1D

ARTICLE RESULTS

|    | Load [ml] | Length [cm] | Leakage [Yes = 1] |
|----|-----------|-------------|-------------------|
| 1  | 25  | 14 | 0 |
| 2  | 25  | 14 | 0 |
| 3  | 50  | 18 | 0 |
| 4  | 50  | 19 | 0 |
| 5  | 75  | 24 | 0 |
| 6  | 75  | 25 | 0 |
| 7  | 75  | 25 | 0 |
| 8  | 100 | 27 | 0 |
| 9  | 100 | 28 | 0 |
| 10 | 125 | 28 | 0 |
| 11 | 125 | 29 | 0 |
| 12 | 150 | 29 | 0 |
| 13 | 150 | 30 | 0 |
| 14 | 175 | 30 | 0 |
| 15 | 175 | 30 | 1 |
| 16 | 175 | 31 | 0 |
| 17 | 175 | 31 | 0 |
| 18 | 175 | 32 | 1 |
| 19 | 200 | 32 | 0 |
| 20 | 200 | 32 | 1 |
| 21 | 200 | 32 | 0 |
| 22 | 200 | 32 | 0 |
| 23 | 225 | 32 | 0 |
| 24 | 200 | 33 | 1 |
| 25 | 225 | 33 | 0 |
| 26 | 225 | 34 | 1 |
| 27 | 225 | 34 | 1 |

Model this data with a Nonlinear Logistic Regression to determine a probability curve that models the probability of leakage based on the length measurement. A sample graph from this modeling is shown in FIG. 7. This probability curve can be used for any of the probabilities of leakage risk described herein.

11. Use the probability curve to correlate locations in the absorbent article with probabilities of leakage. For example, the probability curve can be used to determine a probability of leakage that corresponds with a particular location of Cmin in an absorbent article. As a result, a probability of leakage can be determined for an indicating signal from a secondary indicator disposed at the particular location, under various loadings. As another example, the probability curve can be used to determine a location in absorbent article that corresponds with a particular probability of leakage. As a result, a location for a secondary indicator can be determined in order to indicate the particular probability of leakage, under various loadings. These approaches can be used for any of the probabilities of leakage risk and any of the locations for a secondary wetness indicator described herein.

Figure 7:
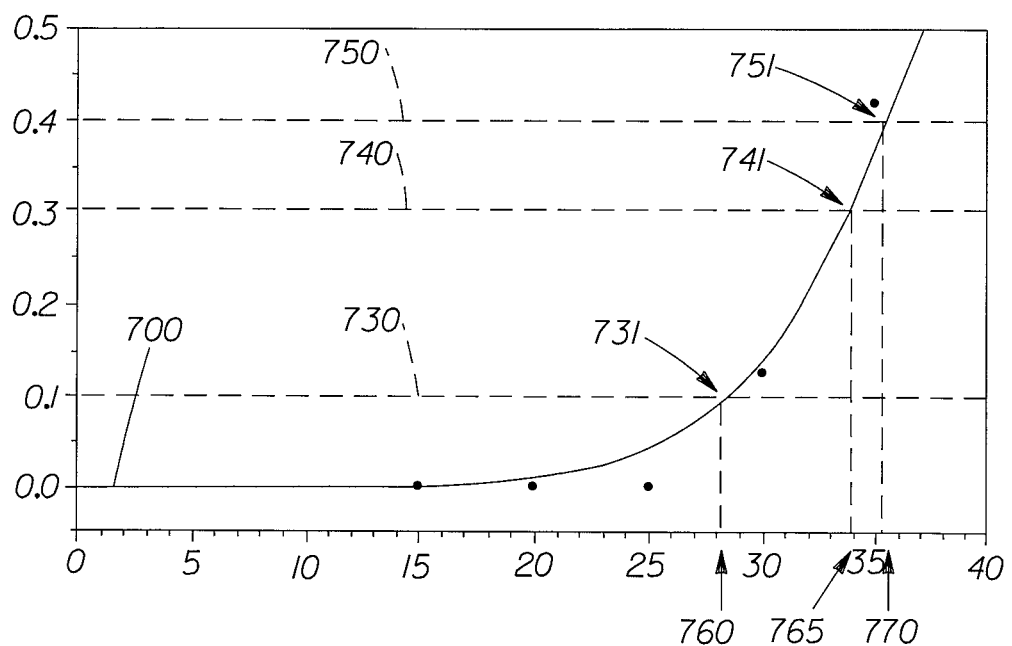
FIG. 7 illustrates an exemplary curve that describes a probability of leakage risk for an absorbent core, according to embodiments of the present disclosure.

In FIG. 7, the probability curve 700 includes points 731, 741, and 751. At point 731, a 10% probability of leakage 730 corresponds with a length 760 of about 28 cm. At point 741, a 30% probability of leakage 740 corresponds with a length 765 of about 34 cm. At point 751, a 40% probability of leakage 750 corresponds with a length 770 of about 35 cm.

Figure 5B:
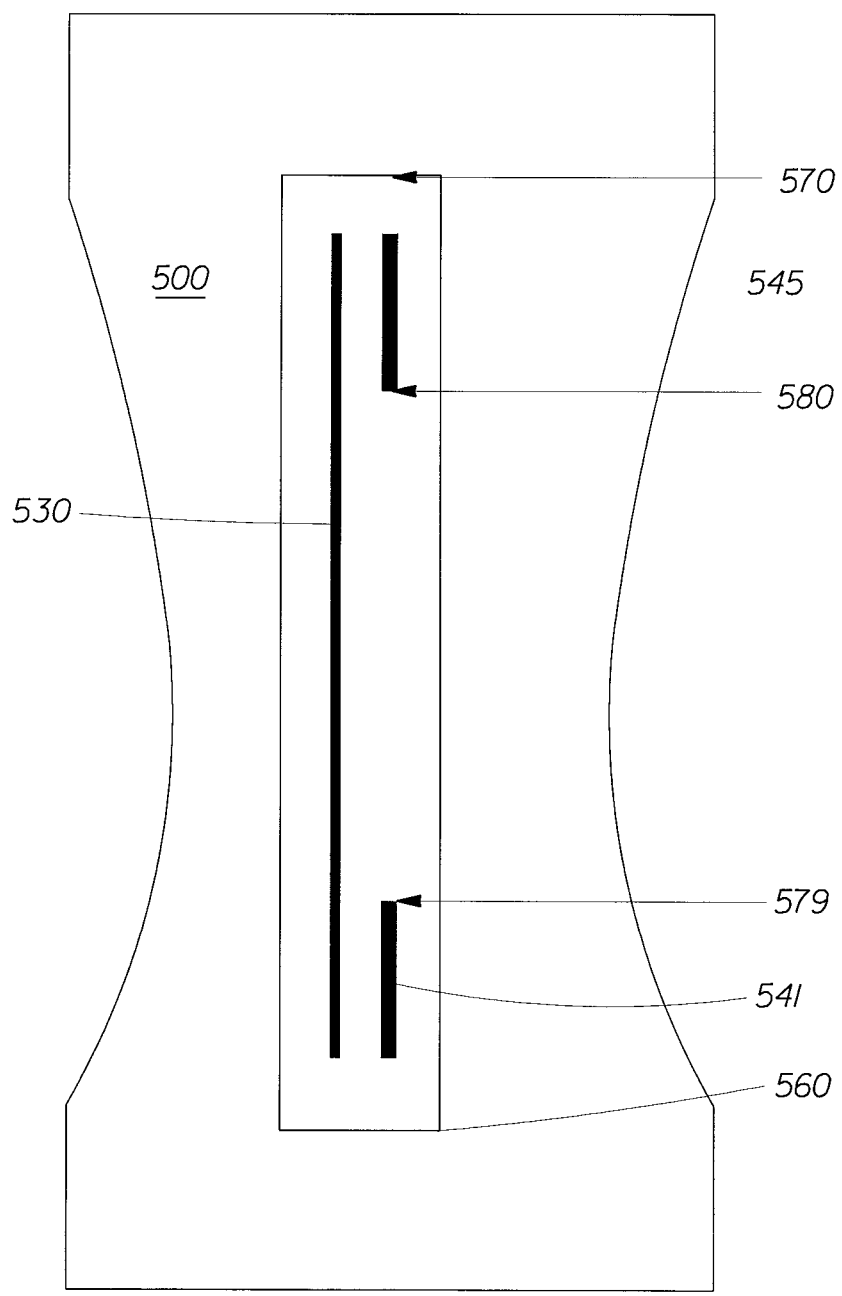
FIG. 5B illustrates a disposable wearable absorbent article having the exemplary loading profile of FIG. 5A, a primary visual fullness indicator, and two secondary visual wetness indicators, according to embodiments of the present disclosure.

FIG. 5B shows a diaper 500 including the absorbent core of FIG. 5A, having the profile 571, front core edge 560, and back core edge 570. The diaper 500 also includes a primary visual fullness indicator 530, a secondary visual wetness indicator 541, and a secondary visual wetness indicator 545. Together, the primary visual fullness indicator 530 and the secondary visual wetness indicators 541 can be considered a visual fullness indicating system. Also, the primary visual fullness indicator 530 and the secondary visual wetness indicators 545, together, can be considered a visual fullness indicating system.

The secondary visual wetness indicator 541 is located within a front of the absorbent article 500 such that an inboard end of the indicator is disposed at the Front Saturation Threshold Location 579. The secondary visual wetness indicator 545 is located within a back of the absorbent article 500 such that an inboard end of the indicator is disposed at the Rear Saturation Threshold Location 580.

Further, the present disclosure contemplates that an absorbent article, such as a disposable wearable absorbent article, can have one or more visual fullness indicators configured as described herein and further configured with various additional and/or alternate structures and/or functions as described below.

One or more embodiments of the present disclosure can be combined with one or more embodiments of U.S. non-provisional patent application Ser. No. 12/346,445 entitled "Disposable Wearable Absorbent Articles with Multiple Indicating Colors," filed on Dec. 30, 2008 and/or US non-provisional patent application entitled "Disposable Wearable Absorbent Articles with Multiple Indicating Colors," filed on Dec. 23, 2009, each of which is incorporated herein by reference. A disposable wearable absorbent article with primary and secondary indicating can also have multiple indicating colors.

One or more embodiments of the present disclosure can be combined with one or more embodiments of U.S. non-provisional patent application Ser. No. 12/346,481 entitled "Absorbent Articles with Multiple Indicating Widths," filed on Dec. 30, 2008 and/or US non-provisional patent application entitled "Absorbent Articles with Multiple Indicating Widths," filed on Dec. 23, 2009, each of which is incorporated herein by reference. A disposable wearable absorbent article with primary and secondary indicating can also have multiple indicating widths.

One or more embodiments of the present disclosure can be combined with one or more embodiments of U.S. non-provisional patent application Ser. No. 12/346,496 entitled "Disposable Wearable Absorbent Articles with Gender Specific Indicia," filed on Dec. 30, 2008 and/or US non-provisional patent application entitled "Disposable Wearable Absorbent Articles with Gender Specific Indicia," filed on Dec. 23, 2009, each of which is incorporated herein by reference. A disposable wearable absorbent article with primary and secondary indicating can also have gender specific indicia.

One or more embodiments of the present disclosure can be combined with one or more embodiments of U.S. non-provisional patent application Ser. No. 12/346,510 entitled "Disposable Wearable Absorbent Articles with Gender Specific Indicating," filed on Dec. 30, 2008 and/or US non-provisional patent application entitled "Disposable Wearable Absorbent Articles with Gender Specific Indicating," filed on Dec. 23, 2009, each of which is incorporated herein by reference. A disposable wearable absorbent article with primary and secondary indicating can also have gender specific indicating.

One or more embodiments of the present disclosure can be combined with one or more embodiments of U.S. non-provisional patent application Ser. No. 12/346,520 entitled "Absorbent Articles with Patterns of Indicating," filed on Dec. 30, 2008 and/or US non-provisional patent application entitled "Absorbent Articles with Patterns of Indicating," filed on Dec. 23, 2009, each of which is incorporated herein by reference. A disposable wearable absorbent article with primary and secondary indicating can also have patterns of indicating.

One or more embodiments of the present disclosure can be combined with one or more embodiments of US non-provisional patent application entitled "Absorbent Articles with Primary and Secondary Indicia," filed on Dec. 23, 2009, which is incorporated herein by reference. A disposable wearable absorbent article with primary and secondary indicating can also have primary and secondary indicia.

The absorbent articles of the present disclosure are easy to understand because they have primary visual fullness indicators and secondary visual wetness indicators. An absorbent article having a primary visual fullness indicator and a secondary visual wetness indicator can help provide certainty about the fullness of the absorbent article. By knowing how full an article is, the article can be changed after the wearer has appropriately utilized the capacity of the article. Also, by knowing how full an article is, the article can be changed before it is likely to leak.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A disposable wearable absorbent article, comprising:
an absorbent core with a total absorbent capacity and an outboard end;
a primary visual fullness indicator;
a center and a lateral centerline; and a secondary visual wetness indicator, having an inboard end and an outboard end;
wherein the secondary visual wetness indicator is spaced apart from the primary visual fullness indicator;
the primary visual fullness indicator's outboard edge is inboard of the secondary visual wetness indicator's outboard edge;
wherein substantially all of the secondary visual wetness indicator is disposed outboard from the outboard end of the absorbent core;
wherein the article further comprises an acquisition layer with an outboard end; a portion of the secondary visual wetness indicator is disposed inboard to the outboard end of the acquisition layer;
the primary visual fullness indicator is disposed offset from the center such that the visual fullness indicator does not overlap with the lateral centerline; and
a portion of the secondary visual wetness indicator is disposed outboard from the outboard end of the acquisition layer.

2. The absorbent article of claim 1, wherein the secondary visual wetness indicator is disposed proximate to the primary visual fullness indicator.

3. The absorbent article of claim 1, wherein the secondary visual wetness indicator is disposed proximate to an outboard end of the primary visual fullness indicator.

4. The absorbent article of claim 1, wherein the inboard end of the secondary visual wetness indicator is disposed outboard from an inboard end of the primary visual fullness indicator.

5. The absorbent article of claim 1, wherein at least a portion of the secondary visual wetness indicator is disposed outboard from an outboard end of the primary visual fullness indicator.

6. The absorbent article of claim 1, wherein substantially all of the primary visual fullness indicator is disposed inboard to the outboard end of the absorbent core.

7. The absorbent article of claim 1, wherein the secondary visual wetness indicator is a fullness indicator.

8. The absorbent article of claim 1, wherein an overall shape of the secondary visual wetness indicator is substantially elongated.

9. The absorbent article of claim 1, wherein an overall length of the primary visual fullness indicator is greater than an overall length of the secondary visual wetness indicator.

10. The absorbent article of claim 1, including an additional secondary visual wetness indicator.

11. A disposable wearable absorbent article, comprising:
an absorbent core with a total absorbent capacity and an outboard end;
an acquisition layer with an outboard end;
a primary visual fullness indicator having an outboard end; and
a secondary visual wetness indicator having an outboard end; and
a center and a lateral centerline;
wherein the secondary visual wetness indicator is disposed longitudinally inboard to a portion of the absorbent core;
wherein the secondary visual wetness indicator is spaced apart from the primary visual fullness indicator;
the primary visual fullness indicator's outboard edge is inboard of the secondary visual wetness indicator's outboard edge;
the primary visual fullness indicator is disposed offset from the center such that the visual fullness indicator does not overlap with the lateral centerline; and
wherein substantially all of the secondary visual wetness indicator is disposed outboard from the outboard end of the acquisition layer.

12. The absorbent article of claim 11, wherein substantially all of the primary visual fullness indicator is disposed inboard to the outboard end of the acquisition layer.

13. A disposable wearable absorbent article, comprising:
an absorbent core with an outboard end;
a distribution layer with an outboard end;
a primary visual fullness indicator having an outboard end;
a center and a lateral centerline; and
a secondary visual wetness indicator that is configured to change to a subsequent visual state when indicating the presence of at least a particular concentration of a bodily exudates, the secondary visual wetness indicator having an outboard end;
wherein the secondary visual wetness indicator is spaced apart from the primary visual fullness indicator;
the primary visual fullness indicator's outboard edge is inboard of the secondary visual wetness indicator's outboard edge;
the primary visual fullness indicator is disposed offset from the center such that the visual fullness indicator does not overlap with the lateral centerline; and
wherein substantially all of the secondary visual wetness indicator is disposed outboard from the outboard end of the distribution layer.

14. The absorbent article of claim 13, wherein substantially all of the primary visual fullness indicator is disposed inboard to the outboard end of the distribution layer.

* * * * *